(12) United States Patent
Verheijen et al.

(10) Patent No.: US 7,897,639 B2
(45) Date of Patent: Mar. 1, 2011

(54) CARBAMOYL ESTERS THAT INHIBIT CHOLINESTERASE AND RELEASE PHARMACOLOGICALLY ACTIVE AGENTS

(75) Inventors: Jeroen C. Verheijen, Cranston, RI (US); ShouCheng Du, Cumberland, RI (US)

(73) Assignee: CoLucid Pharmaceuticals, Inc., Durham, NC (US)

( * ) Notice: Subject to any disclaimer, the term of this patent is extended or adjusted under 35 U.S.C. 154(b) by 405 days.

(21) Appl. No.: 10/969,796

(22) Filed: Oct. 19, 2004

(65) Prior Publication Data
US 2005/0096387 A1  May 5, 2005

Related U.S. Application Data

(60) Provisional application No. 60/512,971, filed on Oct. 21, 2003.

(51) Int. Cl.
*A61K 31/325* (2006.01)
*C07C 271/44* (2006.01)

(52) U.S. Cl. ...................... 514/478; 560/157
(58) Field of Classification Search .............. 560/157; 514/478
See application file for complete search history.

(56) References Cited

U.S. PATENT DOCUMENTS

| | | | |
|---|---|---|---|
| 3,600,427 A | 8/1971 | Verbiscar | |
| 4,791,107 A | 12/1988 | Hamer et al. | 514/228.2 |
| 4,948,807 A * | 8/1990 | Rosin et al. | 514/484 |
| 5,187,165 A | 2/1993 | Hamer et al. | 514/307 |
| 5,302,721 A | 4/1994 | Wong et al. | 548/429 |
| 5,409,948 A | 4/1995 | Greig et al. | 514/411 |
| 5,455,354 A | 10/1995 | Wong et al. | 546/147 |
| 5,538,968 A | 7/1996 | Chiesi et al. | |
| 5,602,176 A | 2/1997 | Enz | 514/490 |
| 5,665,880 A | 9/1997 | Lee et al. | 546/147 |
| 5,677,457 A | 10/1997 | Lee et al. | 546/141 |
| 2007/0275959 A1 | 11/2007 | Verheijen et al. | 514/229.8 |

FOREIGN PATENT DOCUMENTS

| | | |
|---|---|---|
| AU | 2002226687 | 8/2002 |
| DE | 38 05 744 A1 | 9/1988 |
| EP | 0513703 A2 | 11/1992 |
| FR | 2 719 047 A1 | 10/1995 |
| JP | 03002155 | 1/1991 |
| WO | WO 96/02524 A1 | 2/1996 |
| WO | WO 97/14694 | 4/1997 |
| WO | WO-97/22339 A1 | 6/1997 |
| WO | WO 97/23484 | 7/1997 |
| WO | WO-00/25821 A1 | 5/2000 |
| WO | WO-2004/034963 A2 | 4/2004 |

OTHER PUBLICATIONS

White et al. "On the Physostigmine-Like Action of Certain Synthetic Urethanes" J. Pharmacol. 1931, vol. 41, pp. 259-288.*

Patani et al. "Bioisosterism: A Rational Approach in Drug Design" Chemical Reviews, 1996, vol. 96, pp. 3147-3176.*
Tumiatti et al. "[4-[[N-(3-Chlorophenyl)carbamoyl]oxy]-2-butynyl]trimethylammonium (McN-A-343)-Related Compounds. Effect on the Butynyl Chain Inclusion into an Aromatic Unit on the Potency for Muscarinic Receptors" Bioorganic & Medicinal Chemistry, 2000, vol. 8, pp. 681-689.*
Amstutz et al., "Cyclische Phenyl-carbamate des Miotin-Typs und ihre Wirkung auf die Acetylcholinesterase", *Helvetica Chimica Acta*, 73:739-753 (1990) (English Abstract Only).
Brossi et al., "Invited Review. Phenserine, a Novel Anticholinesterase Related to Physostigmine: Total Synthesis and Biological Properties", *Aust. J. Chem.*, 49:171-181 (1996).
Cutler et al., "Muscarinic $M_1$-Receptor Agonists: Potential in the Treatment of Alzheimer's Disease",*CNS Drugs*, 3(6):467-481 (1995).
Database CA [Online] Chemical Abstracts Service, Columbus, Ohio, Koyama et al., "Pharmaceuticals containing (hydroxybenzyl) amines as acetylcholine esterase inhibitors and selective serotonin reuptake inhibitors", XP002331878 retrieved from STN Database accession No. 2004:291183 abstract & JP 2004 107322 A2 (BTG International Ltd., UK) Apr. 8, 2004.
Database CA [Online] Chemical Abstracts Service, Columbus, Ohio, Goto et al., "Preparation of aromatic carbamates as choline esterase inhibitors for improvement of cerebral function", XP002331879 retrieved from STN Database accession No. 1991:206818 abstract & JP 03 002155 A2 (Takeda Chemical Industries, Ltd., Japan) Jan. 8, 1991.
Database Beilstein, Beilstein Institut Fuer Chemische Wissenschaften, Frankfurt Am Main, DE, XP002331880.
De Sarno et al., "The Effect of Heptyl-Physostigmine, a New Cholinesterase Inhibitor, on the Central Cholinergic System of the Rat", *Neurochem. Res.*, 14(10):971-977 (1989).
Elmalem et al., "Antagonism of Morphine-Induced Respiratory Depression by Novel Anticholinesterase Agents", *Neuropharmacol.*, 30(10):1059-1064 (1991).

(Continued)

*Primary Examiner* — Joseph R Kosack
(74) *Attorney, Agent, or Firm* — Ivor R. Elrifi; Heidi A. Erlacher; Mintz, Levin, Cohn, Ferris, Glovsky and Popeo, P.C.

(57) ABSTRACT

Carbamoyl esters inhibit cholinesterase activity and, upon hydrolysis release a pharmacologically active agent. In one embodiment, the carbamoyl ester has the following structure:

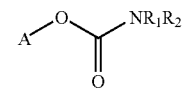

wherein A is selected from the group consisting of an unsubstituted aryl, a substituted aryl, an unsubstituted heteroaryl and a substituted heteroaryl. The carbamoyl esters are employed in methods to treat an individual. The pharmacologically active agent obtained by hydrolysis of the carbamoyl esters can treat, for example, a nervous system condition, a cholinergic deficiency and conditions or diseases associated with a deficiency in a pharmacologically active agent, such as acetylcholine.

15 Claims, 1 Drawing Sheet

OTHER PUBLICATIONS

Froestl et al., "SGS742: the first GABA$_B$ receptor antagonist in clinical trials", *Biochem. Pharmacol.*, 68:1479-1487 (2004).

Gatto et al., "TC-1734: An Orally Active Neuronal Nicotinic Acetylcholine Receptor Modulator with Antidepressant, Neuroprotective and Long-Lasting Cognitive Effects", *CNS Drug Reviews*, 10(2):147-166 (2004).

Heinonen et al., "Desmethylselegiline, a Metabolite of Selegiline, Is an Irreversible Inhibitor of Monoamine Oxidase Type B in Humans", *J. Clin. Pharmacol.*, 37:602-609 (1997).

Janssen et al., "Does phenylethylamine act as an endogenous amphetamine in some patients?", *Int. J. Neuropsychopharmacol.*, 2:229-240 (1999).

Kerr et al., "GABA$_B$ Receptors", *Pharmac. Ther.*, 67(2):187-246 (1995).

Korczyn, A.D., "Muscarinic M$_1$ agonist in the treatment of Alzheimer's disease", *Exp. Opin. Invest. Drugs*, 9(10):2259-2267 (2000).

Kupsch, A., "Rasagiline Teva Pharmaceutical", *Curr. Opin. Investig. Drugs*, 3(5):794-979 (2002).

Land et al., "D-Cycloserine: Effects on Long-Term Retention of a Conditioned Response and on Memory for Contextual Attributes", *Neurobiol. Learning Mem.*, 72(3):158-168 (1999).

Lipiello et al., "RJR-2403 is an Efficacious Agonist for Human β4α2 Neuronal Nicotinic Acetylcholine Receptors with Lower Efficacy for Other Human Receptor Subtypes", *Soc. Neurosci.*, 24:88 (Abstract 39.26) (1998).

Obinu et al., "Brain Selective Stimulation of Nicotinic Receptors by RJR 1734 Enhances ACh Transmission From Frontoparietal Cortex and Enhances Memory in Rodents", *Internatl. J. Neuropyschopharamology*, 3(Suppl. 1):S361 (2003) (Abstract Only).

Obinu et al., "Brain Selective Stimulation of Nicotinic Receptors by TC-1734 Enhances Ach Transmission From Frontoparietal Cortex and Enhances Memory in Rodents", *Progress Neuropsychopharmacol. Biol. Psychiatry*, 26:913-918 (2002).

Parsons et al., "Memantine is a clinically well tolerated *N*-methyl-D-aspartate (NMDA) receptor antagonist—a review of preclinical data", *Neuropharmacol.*, 38(5):735-767 (1999).

Rampa et al., "Acetylcholinesterase Inhibitors: SAR and Kinetic Studies on ω-[N-Methyl-N-(3-alkylcarbamoyloxyphenyl)methyl]aminoalkoxyaryl Derivatives", *J. Med. Chem.*, 44:3810-3820 (2001).

Sterling et al., "Novel Dual Inhibitors of AChE and MAO Derived from Hydroxy Aminoindan and Phenethylamine as Potential Treatment for Alzheimer's Disease",*J. Med. Chem.*, 45:5260-5279 (2002).

Trabace et al., "CHF2819: Pharmacological Profile of a Novel Acetylcholinesterase Inhibitor", *CNS Drug Reviews*, 8(1):53-69 (1992).

Tumiatti et al., "[4-[[N-(3-Chlorophenyl)carbamoyl]oxy]-2-butynyl]-trimethylammonium (McN-A-343)-Related Compounds. Effect of the Butynyl Chain Inclusion into an Aromatic Unit on the Potency for Muscarinic Receptors", *Bioorg. Med. Chem.*, 8:681-689 (2000).

Yang et al., "β-Phenylethylamine: A Specific Substrate for Type B Monoamine Oxidase of Brain", *J. Pharmacol. Exp. Ther.*, 187(2):365-371 (1973).

Fogelson et al., "Effects of rivastigmine on the quantitative EEG in demented Parkinsonian patients", *Acta Neurol. Scand.*, 107(4):252-255 (2003).

Grace et al., "A comparison of sleep profiles in patients with dementia with Lewy bodies and Alzheimer's disease", *Int J. Geriatr. Psychiatry*, 15(11):1028-1033 (2000).

Schredl et al., "The effect of rivastigmine on sleep in elderly healthy subjects", *Experimental Gerontol.*, 35(2):243-249 (2000).

Siatra-Papastaikoudi, T., et al., "Synthesis of Carbamate Esters of Phenethylamines and their Pharmacological Action on the Central Nervous System", *Chimika Chronika*, 10(4), 307-13 (1981).

\* cited by examiner

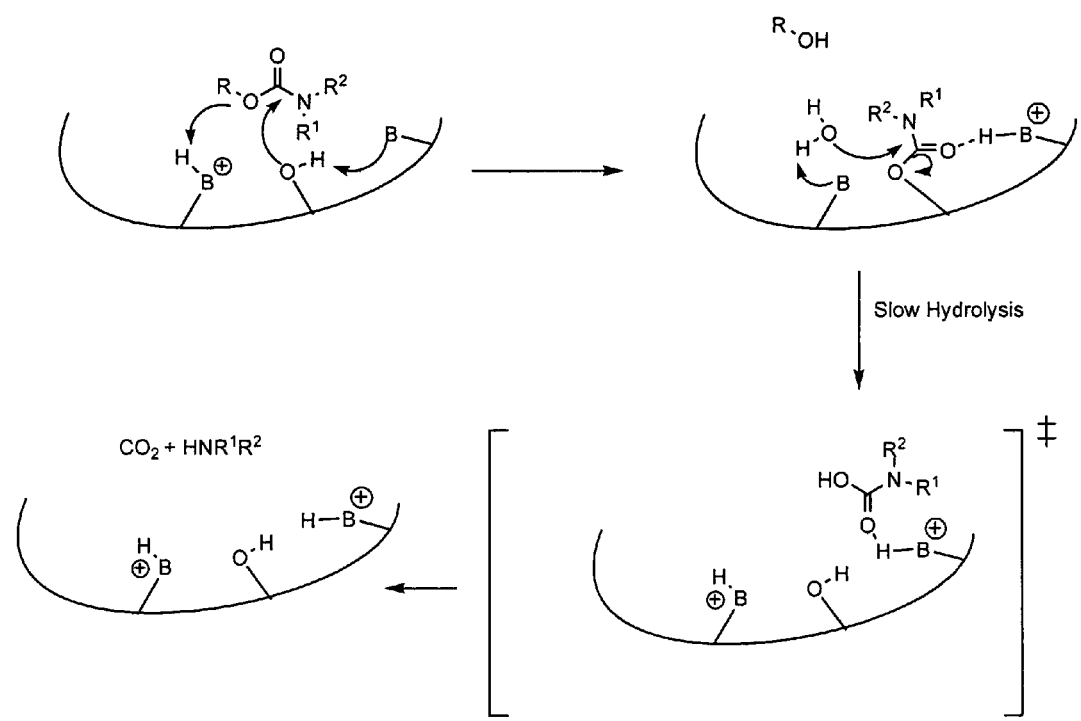

CARBAMOYL ESTERS THAT INHIBIT CHOLINESTERASE AND RELEASE PHARMACOLOGICALLY ACTIVE AGENTS

RELATED APPLICATION

This application claims the benefit of U.S. Provisional Application No. 60/512,971, filed Oct. 21, 2003. The entire teachings of the above application are incorporated herein by reference.

BACKGROUND OF THE INVENTION

A number of conditions and diseases in humans are accompanied by or are a consequence of disruptions in cell signal molecules. For example, there can be inadequate synthesis, release or re-uptake of the cell signal molecule(s), or disruptions in mediating cellular signaling of the molecule(s) by receptor or non-receptor mechanisms that result in a disease or other condition. In many instances, clinical management strategies and currently available drugs are frequently associated with adverse side effects and must be meticulously monitored in patients. Current strategies to develop drugs to treat conditions and diseases that are accompanied by or are a consequence of disruptions in cell signal molecules require significant structure-activity modification of a compound. In addition, currently available drugs generally do not target the drug to particular cells or tissues and fail to result in delivery of a drug with a long-lasting effect. In many instances, correction of disruptions in a single cell signal molecule does not effectively treat symptoms of the disease or condition. Thus, there is a need to develop new, improved and effective methods of treatment for diseases or conditions that are associated with or are accompanied by disruptions in cell signal molecules.

SUMMARY OF THE INVENTION

The present invention is directed to carbamoyl esters that have cholinesterase inhibitory activity and comprise an amine group that, upon hydrolysis, become at least a component of a pharmacologically active agent. The invention is also directed to methods of using the carbamoyl esters and to pharmaceutical compositions of the carbamoyl esters.

In one embodiment, the invention is a carbamoyl ester that inhibits a cholinesterase, comprising an amine group that, upon hydrolysis, becomes at least a component of a pharmacologically active agent.

In another embodiment, the invention is a carbamoyl ester having the following structure:

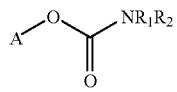

wherein A is selected from the group consisting of an unsubstituted aryl, a substituted aryl, an unsubstituted heteroaryl and a substituted heteroaryl; and $R_1$ and $R_2$ are each, independently or in combination, selected from the group consisting of a hydrogen, an unsubstituted alkyl, a substituted alkyl, an unsubstituted aralkyl, a substituted aralkyl, an unsubstituted heteroalkyl, a substituted heteroalkyl, an unsubstituted heteroaralkyl, a substituted heteroaralkyl, an unsubstituted aryl, a substituted aryl, an unsubstituted heteroaryl, a substituted heteroaryl, an unsubstituted cycloalkyl, a substituted cycloalkyl, an unsubstituted heterocycloalkyl and a substituted heterocycloalkyl.

In a further embodiment, the invention is a carbamoyl ester that is not (3aS-cis)-1,2,3,3a,8,8a-hexahydro,-1,3a,8-trimethyl pyrrolo[2,3-b]-indo-5-ol, 4-pyridinyl carbamate ester, (3aS-cis)-1,2,3,3a,8,8a-hexahydro-1,3a,8-trimethyl-pyrolo[2,3-b]indol-5-ol,(2-phenyl)ethyl carbamate ester, (3aS-cis)-1,2,3,3a,8,8a-hexahydro-1,3a,8-trimethyl-pyrolo[2,3-b]indol-5-ol[1-(1-naphthyl)ethyl]carbamate ester, 7-bromo-(3aS-cis)-1,2,3,3a,8,8a-hexahydro-1,3a,8-trimethyl pyrrolo[2,3-b]indol-5-ol,-heptyl carbamate ester, or a tetrahydroisoquinolinyl carbamate ester.

In an additional embodiment, the invention is a carbamoyl ester selected from the group consisting of:

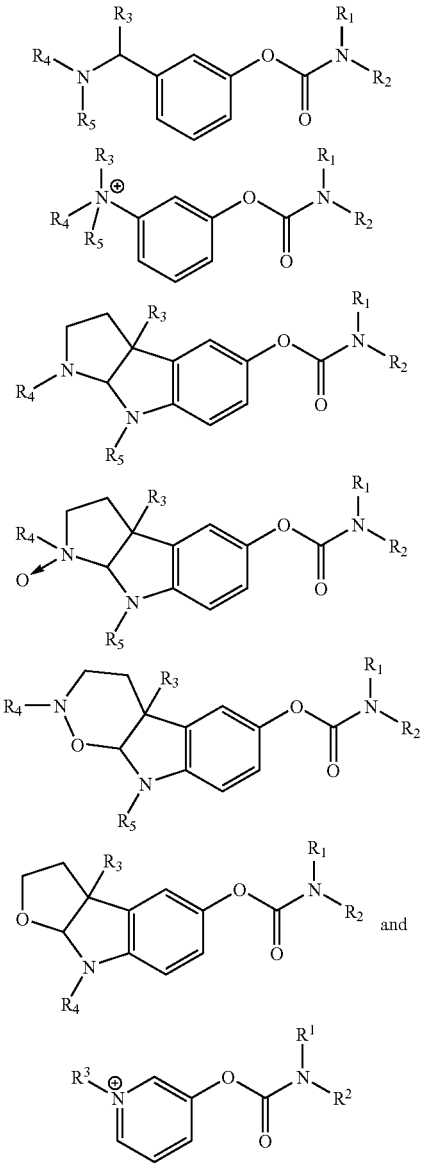

wherein $R_3$, $R_4$ and $R_5$ are each, independently or in combination, selected from the group consisting of a hydrogen, an unsubstituted alkyl, a substituted alkyl, an unsubstituted aralkyl, a substituted aralkyl, an unsubstituted heteroalkyl, a substituted heteroalkyl, an unsubstituted heteroaralkyl, a substituted heteroaralkyl, an unsubstituted aryl, a substituted aryl, an unsubstituted heteroaryl, a substituted heteroaryl, an unsubstituted cycloalkyl, a substituted cycloalkyl, an unsubstituted heterocycloalkyl and a substituted heterocycloalkyl.

In still another embodiment, the invention is a carbamoyl ester selected from the group consisting of:

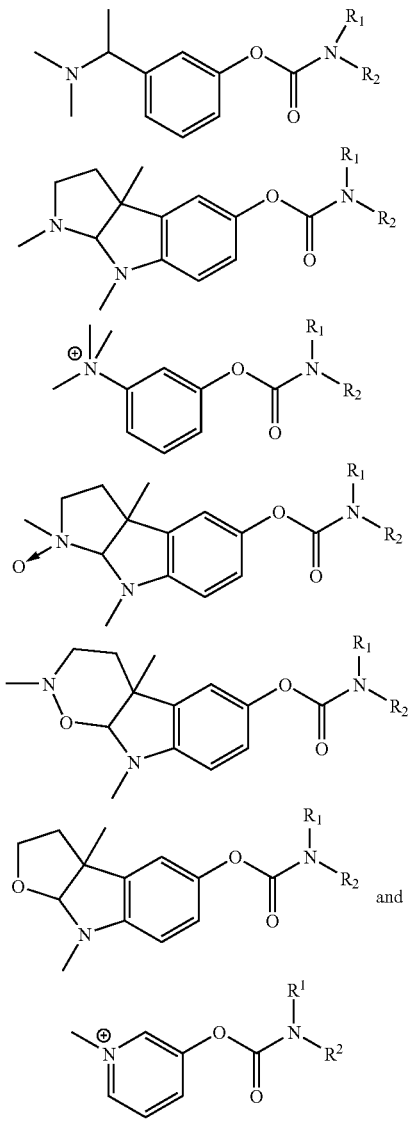

In yet another embodiment, the invention is a method of treating an individual, comprising the step of administering to the individual a carbamoyl ester, wherein the carbamoyl ester inhibits a cholinesterase and includes an amine group that, upon hydrolysis, becomes at least a component of a pharmacologically active agent that treats the individual for a condition of the individual.

In an additional embodiment, the invention is a method of treating a nervous system condition in an individual, comprising the step of administering to the individual a carbamoyl ester, wherein the carbamoyl ester inhibits a cholinesterase thereby treating the nervous system condition in the individual and wherein the carbamoyl ester includes an amine group that, upon hydrolysis, becomes at least a component of a pharmacologically active agent that further treats the nervous system condition in the individual.

In a further embodiment, the invention is a method of treating a central nervous system condition in an individual, comprising the step of administering to the individual a carbamoyl ester that inhibits acetylcholinesterase thereby treating the central nervous system condition in the individual, wherein the carbamoyl ester includes an amine group that, upon hydrolysis, becomes at least one component of a pharmacologically active agent, wherein the pharmacologically active agent is selected from the group consisting of an amphetamine compound and a methamphetamine compound, whereby the pharmacologically active agent further treats the central nervous system condition in the individual.

An additional embodiment of the invention is a method of increasing acetylcholine in an individual, comprising the step of administering to the individual a carbamoyl ester in the individual, wherein the carbamoyl ester inhibits a cholinesterase, thereby increasing acetylcholine and includes an amine group that, upon hydrolysis, becomes at least a component of a pharmacologically active agent that further increases acetylcholine in the individual.

In a further embodiment, the invention is a method of increasing acetylcholine in an individual, comprising the step of administering to the individual a carbamoyl ester that inhibits acetylcholinesterase, thereby increasing acetylcholine in the individual, wherein the carbamoyl ester includes an amine group that, upon hydrolysis, becomes at least one component of a pharmacologically active agent, wherein the pharmacologically active agent is selected from the group consisting of an amphetamine compound and a methamphetamine compound.

In still an additional embodiment, the invention is a method of treating a cholinergic deficiency in an individual, comprising the step of administering to the individual a carbamoyl ester, wherein the carbamoyl ester inhibits a cholinesterase thereby treating the cholinergic deficiency in the individual, and wherein the carbamoyl ester includes an amine group that, upon hydrolysis, becomes at least a component of a pharmacologically active agent that further treats the cholinergic deficiency in the individual.

In yet another embodiment, the invention is a method of treating an impairment in memory in an individual, comprising the step of administering to the individual a carbamoyl ester, wherein the carbamoyl ester inhibits a cholinesterase thereby treating the impairment in memory in the individual, and wherein the carbamoyl ester includes an amine group that, upon hydrolysis, becomes at least a component of a pharmacologically active agent that further treats the impairment in memory in the individual.

In another embodiment, the invention is a method of delivering a pharmacologically active agent to a tissue, comprising the step of administering to the tissue a carbamoyl ester, wherein the carbamoyl ester inhibits a cholinesterase and includes an amine group that, upon hydrolysis, becomes at least a component of a pharmacologically active agent, thereby delivering the pharmacologically active agent to the tissue.

In yet another embodiment, the invention is a pharmaceutical composition comprising a carbamoyl ester that inhibits a cholinesterase, wherein the carbamoyl ester includes an amine group that, upon hydrolysis, becomes at least a component of a pharmacologically active agent.

The invention described herein provides carbamoyl esters that inhibit the activity of a cholinesterase and, upon hydrolysis, become a least a component of a pharmacologically active agent. Methods of using the carbamoyl esters can, for example, treat neurological conditions, increase the amount of an amine in a synaptic cleft, treat a cholinergic deficiency and increase transmission between neurons, deliver amines into a synaptic cleft and increase delivery of pharmacologically active amines into the central nervous system. Advantages of the claimed invention include, for example, delivering a pharmacologically active agent, such as modulators of neurotransmission, without significant structural alteration to the pharmacologically active agent, to a synapse, which leads to neurotransmission that may be lacking or diminished, thereby, treating diseases or conditions associated with neurotransmitter imbalances. The method of the invention, by employing the carbamoyl esters, can increase the amount of a pharmacologically active agent, such as a neurotransmitter, thereby compensating for a disease or condition associated with deficiency of a neurotransmitter.

Thus, the carbamoyl esters of the invention can be employed in the treatment of diseases or other conditions associated with pharmacologically active agents and thereby halt, reverse or diminish the progression of the diseases or other conditions, or promote physiological processes that can be treated with pharmacologically active agents, such as pharmacologically active agents that treat conditions associated with synaptic transmission.

BRIEF DESCRIPTION OF THE DRAWINGS

The FIGURE depicts the mechanism of acetylcholinesterase inhibition by the carbamoyl esters of the invention.

DETAILED DESCRIPTION OF THE INVENTION

The features and other details of the invention, either as steps of the invention or as combinations of parts of the invention, will now be more particularly described and pointed out in the claims. It will be understood that the particular embodiments of the invention are shown by way of illustration and not as limitations of the invention. The principle features of this invention can be employed in various embodiments without departing from the scope of the invention.

In one embodiment, the invention is a carbamoyl ester that inhibits a cholinesterase, comprising an amine group that, upon hydrolysis, becomes at least a component of a pharmacologically active agent. The term "carbamoyl ester," as used herein, refers to a carbamoyl compound that has the following structural formula:

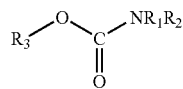

I wherein $R_1$ and $R_2$ each, independently or in combination, are hydrogen or a hydrocarbon and wherein $R_3$ is a hydrocarbon. In particular, the carbamoyl ester inhibits a cholinesterase by competing with a compound (e.g., acetylcholine (ACh)) that binds to the cholinesterase. As shown in the FIGURE, the carbamoyl ester binds to the cholinesterase to form a carbamoylated enzyme. The cholinesterase is inhibited when it is prevented from inactivating a compound, such as the neurotransmitter ACh, to any degree that cholinesterase would act on the neurotransmitter in the absence of the carbamoyl ester. Hydrolysis of the carbamoylated enzyme is much slower than that of, for example, an acetylated enzyme, which is formed by hydrolysis of its endogenous substrate acetylcholine. Inhibition of the cholinesterase by a carbamoyl ester molecule ceases when the carbamoylated enzyme is hydrolyzed. Upon hydrolysis of the carbamoylated enzyme, a released compound, such as an amine, becomes at least a component of a pharmacologically active agent.

Hydrolysis of the carbamoyl ester comprising an amine group, to become at least a component of a pharmacologically active agent, can be hydrolysis by an enzyme (e.g., a cholinesterase) or hydrolysis by other than an enzyme, such as by an acid (e.g., gastric acid). In one embodiment, the carbamoyl ester that inhibits a cholinesterase, comprises an amine group that, upon hydrolysis by reaction with the cholinesterase, becomes at least a component of a pharmacologically active agent.

The phrase "upon hydrolysis by reaction with an enzyme," as used herein, refers to the two-step process of reaction of the carbamoyl ester with an enzyme to form a carbamoylated enzyme, and decomposition of the carbamoylated enzyme by reaction with $H_2O$.

Likewise, the phrase "upon hydrolysis by reaction with the cholinesterase," as used herein, refers to the two-step process of reaction of the carbamoyl ester with the enzyme cholinesterase, to form a carbamoylated enzyme, and decomposition of the carbamoylated enzyme by reaction with $H_2O$.

The cholinesterase inhibited by the carbamoyl ester of the invention can be, for example, at least one member selected from the group consisting of an acetylcholinesterase (AChE) or a butyrylcholinesterase (BuChE). The carbamoyl ester can inhibit ACHE alone, BuChE alone, or can inhibit both ACHE and BuChE to similar or different degrees.

ACHE is located on excitable membranes and inactivates ACh. The excitable membrane can be a presynaptic neuron or a postsynaptic neuron. ACHE is also referred to as specific cholinesterase. BuChE is located on excitable membranes and non-neuronal tissue such as blood cells (Darvesh, S. et al., *Nature Reviews* 4: 131-138 (2003), the teachings of which are hereby incorporated by reference in its entirety). BuChE is also referred to as pseudocholinesterase or nonspecific cholinesterase. ACHE and BuChE are regulators of cholinergic neurotransmission in the central nervous system (brain and spinal cord), peripheral nervous system and autonomic nervous system (parasympathetic nervous system and sympathetic nervous system).

Upon hydrolysis of the carbamate bond of the carbamoylated enzyme, a released compound, such as a compound that includes an amine, becomes at least a component of a pharmacologically active agent. The term "becomes at least a component of a pharmacologically active agent," as used herein, refers to the release of a compound, such as an amine-containing compound, as a consequence of hydrolysis of the carbamoylated enzyme. The compound released by hydrolysis of the carbamoylated enzyme is at least a portion of a pharmacologically active agent. In one embodiment, the compound released by the hydrolysis of the carbamoylated enzyme is a prodrug. The term "prodrug," as used herein, refers to a compound, such as a carbamoyl ester of the invention, that is administered, but is not the actual drug desired in the treatment regimen and is transformed by metabolic processes to the actual drug desired in the treatment. The prodrug then can be modified to release a pharmacologically active agent. In another embodiment, the compound released by hydrolysis of the carbamoylated enzyme can, itself, be the pharmacologically active agent. Thus, a carbamoyl ester of the invention has a dual role as an inhibitor of a cholinesterase and as a delivery vehicle for a pharmacologically active agent.

The term "pharmacologically active agent," as used herein, refers to a compound that influences biological processes by altering the activity, localization and/or expression of molecules (e.g., neurotransmitters, peptides, proteins) which are directly or indirectly involved in the biological processes.

The pharmacologically active agent can be a phenylethylamine, such as an amphetamine compound (l-amphetamine, d-amphetamine, l-methamphetamine, d-methamphetamine, or any mixture of the d- and l-isomers of amphetamine and methamphetamine). The pharmacologically active agent can be a prodrug or precursor that metabolizes into a compound that contains a primary or secondary amine of a pharmacologically active agent, such as deprenyl that metabolizes into desmethylselegline, l-amphetamine and l-methamphetamine.

The pharmacologically active agent preferably alters biological processes in a manner which results in a desirable effect, for example, to improve biological processes, alleviate impairments or disease symptoms, or to slow and/or reverse disease progression. For example, upon hydrolysis of the carbamoyl ester, the released amine can become at least a component of a pharmacologically active agent that increases the amount of a neurotransmitter in a synapse by diminishing or halting the breakdown of a neurotransmitter, by participating in cellular events that result in the release of additional neurotransmitters, by inhibiting the re-uptake of a neurotransmitter, and/or by increased synthesis of a neurotransmitter.

The pharmacologically active agent can, for example, result in an increase in ACh in the synapse of central nervous system neurons which can compensate for the cholinergic deficiency, for example, in Alzheimer's patients, thereby promoting neuronal transmission to ultimately alleviate or ameliorate the symptoms of Alzheimer's disease. Alzheimer's disease is accompanied by symptoms that include cognitive impairment, disoriented behavior, alter personality, difficulty speaking and comprehending and impaired gait and movement. It has been suggested that decreased cholinergic function is responsible for the symptoms of Alzheimer's disease (Benzi, G., et al., *European J. Pharmacol.* 346:1-13 (1998); Korczyn, A. D., *Exp. Opin. Invest. Drugs* 9:2259-2267 (2000)).

The decrease in cholinergic function can be a decrease in the amount of ACh synthesized or released, the inability of a neuron to respond to ACh or inactivation of AChE. In Alzheimer's disease, current treatments include the administration of compounds which increase cholinergic signaling (Jann, M. W., *Pharmacotherapy* 20:1-12 (2000); Bachurin, S. O., *Med. Res. Rev.* 23:48-88 (2003)). However, these compounds have modest efficacy, low response rate (typically about 30%-50%) and numerous side effects such as nausea, gastrointestinal problems and fatigue. In one embodiment, the carbamoyl esters of the invention inhibit ACHE and, upon hydrolysis, become at least a component of a pharmacologically active agent that increases neurotransmitters, such as ACh, in the synapse of the central nervous system neurons. Thus, for example, the carbamoyl esters of the invention inhibit ACHE, which degrades ACh in the synapses of neurons in Alzheimer's patients, and release pharmacologically active agents, which, collectively or individually, increase neurotransmitters in the synapses.

Cholinergic deficiencies also characterize other disorders such as Parkinson's disease, progressive supranuclear palsy, vascular dementia and Down's syndrome (Korczyn, A. D., *Exp. Opin. Invest. Drugs* 9:2259-2267 (2000)). Thus, the carbamoyl esters of the invention can also be employed to increase the ACh in these disorders.

Likewise, the pharmacologically active agent can result in an increase in the neurotransmitter dopamine in the central nervous system of patients with Parkinson's disease, thereby promoting neuronal transmission to thereby diminish the symptoms of Parkinson's disease. The increase in dopamine can be a direct result of the hydrolysis of the carbamoylated enzyme to deliver dopamine as a pharmacologically active agent, or an indirect result of hydrolysis of the carbamoylated enzyme to deliver a pharmacologically active agent which results in an increase in dopamine in synapses by, for example, inhibiting the re-uptake of dopamine, preventing the breakdown of dopamine, increasing the release of dopamine or be a precursor (e.g., L-DOPA) in the synthesis of dopamine.

Thus, the pharmacologically active agent can be a central nervous system-type (brain, spinal cord) pharmacologically active agent. The term "central nervous system-type," as used herein, refers to a pharmacologically active agent that has an effect in the central nervous system.

The pharmacologically active agent can also be a peripheral nervous system-type pharmacologically active agent or an autonomic nervous system-type (parasympathetic nervous system and sympathetic nervous system) pharmacologically active agent. The terms "peripheral nervous system-type" and "autonomic nervous system-type," as used herein, refers to a pharmacologically active agent that has an effect in the peripheral nervous system and the autonomic nervous system, respectively.

The pharmacologically active agent can include a prodrug and other structural (e.g., isomers or stereoisomers, such as d, l, dl, R, S, and RS stereoisomers) and functional derivatives thereof in which, preferably, a primary or secondary amine is available for substitution.

In another embodiment, the carbamoyl ester has the following structure:

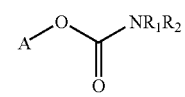

wherein A is selected from the group consisting of an unsubstituted aryl, a substituted aryl, an unsubstituted heteroaryl and a substituted heteroaryl; and $R_4$ and $R_2$ are each, independently or in combination, selected from the group consisting of a hydrogen, an unsubstituted alkyl, a substituted alkyl, an unsubstituted aralkyl, a substituted aralkyl, an unsubstituted heteroalkyl, a substituted heteroalkyl, an unsubstituted heteroaralkyl, a substituted heteroaralkyl, an unsubstituted aryl, a substituted aryl, an unsubstituted heteroaryl, a substituted heteroaryl, an unsubstituted cycloalkyl, a substituted cycloalkyl, an unsubstituted heterocycloalkyl and a substituted heterocycloalkyl.

The term "alkyl," used alone or as part of a larger moiety, includes both straight, branched, or cyclic saturated hydrocarbon chains containing one to twelve carbon atoms.

A heteroalkyl, as used herein, is an alkyl group in which one or more carbon atoms is replaced by a heteroatom.

The term "aryl," used alone or as part of a larger moiety as in "aralkyl" or "aralkoxy," are carbocyclic aromatic ring systems (e.g. phenyl), fused polycyclic aromatic ring systems (e.g., naphthyl and anthracenyl) and aromatic ring systems fused to carbocyclic non-aromatic ring systems (e.g., 1,2,3, 4-tetrahydronaphthyl and indanyl) having five to about fourteen carbon atoms.

The term "heteroaryl," used alone or as part of a larger moiety as in "heteroaralkyl" or "heteroarylalkoxy," refers to aromatic ring system having five to fourteen members and having at least one heteroatom. Preferably a heteroaryl has from one to about four heteroatoms. Preferred heteroalkyls are those wherein the heteroatom is selected from the groups consisting of oxygen, sulfur, nitrogen, phosphorase and halides. Examples of heteroaryl rings include pyrazolyl, furanyl, imidazolyl, isoxazolyl, oxadiazolyl, oxazolyl, pyrrolyl, pyridyl, pyrimidinyl, purinyl, pyridazinyl, pyrazinyl, thiazolyl, thiadiazolyl, isothiazolyl, triazolyl, thienyl, 4,6-dihydro-thieno[3,4-c]pyrazolyl, 5,5-dioxide-4,6-dihydrothieno[3,4-c]pyrazolyl, thianaphthenyl, 1,4,5,6,-tetrahydrocyclopentapyrazolyl, carbazolyl, benzimidazolyl, benzothienyl, benzofuranyl, indolyl, azaindolyl, indazolyl, quinolinyl, benzotriazolyl, benzothiazolyl, benzothiadiazolyl, benzooxazolyl, benzimidazolyl, isoquinolinyl, isoindolyl, acridinyl, and benzoisazolyl. Preferred heteroaryl groups are pyrazolyl, furanyl, pyridyl, quinolinyl, indolyl and imidazolyl.

An aralkyl group, as used herein, is an aryl substituent that is linked to a compound by a straight chain or branched alkyl group having from one to twelve carbon atoms.

An heterocycloalkyl group, as used herein, is a heterocycle substituent that is linked to a compound by a straight chain or branched alkyl group having from one to twelve carbon atoms.

An heteroaralkyl group, as used herein, is a heteroaryl substituent that is linked to a compound by a straight chain or branched alkyl group having from one to twelve carbon atoms.

An aryl (including aralkyl, aralkoxy and the like) or heteroaryl (including heteroaralkyl and heteroaralkoxy and the like) may contain one or more substituents. Examples of suitable substituents include aliphatic groups, aryl groups, haloalkoxy groups, heteroaryl groups, halo and hydroxy.

In an additional embodiment, the carbamoyl ester is not (3aS-cis)-1,2,3,3a,8,8a-hexahydro,-1,3a,8-trimethyl pyrrolo[2,3-b]-indo-5-ol, 4-pyridinyl carbamate ester, (3aS-cis)-1,2,3,3a,8,8a-hexahydro-1,3a,8-trimethyl-pyrolo[2,3-b]indol-5-ol,(2-phenyl)ethyl carbamate ester, (3aS-cis)-1,2,3,3a,8,8a-hexahydro-1,3,8-trimethyl-pyrolo[2,3-b]indol-5-ol[1-(1-naphthyl)ethyl]carbamate ester, 7-bromo-(3aS-cis)-1,2,3,3a,8,8a-hexahydro-1,3a,8-trimethyl pyrrolo[2,3-b]indol-5-ol, n-heptyl carbamate ester, or a tetrahydroisoquinolinyl carbamate ester.

Examples of aromatic carbamoyl esters are described in Brossi, A., et al, *Aust. J. Chem.* 49:171-181 (1996); Trabace, L., et al., *CNS Drug Reviews* 8:53-69 (2992); DeSarno, P., et al., *Neurochem. Res.* 14:971-977 (1989), U.S. Pat. Nos. 4,791,107; 4,948,807; 5,187,165; 5,302,721; 5,409,948; 5,455,354; 5,602,176; 5,665,880; 5,677,457; WO 97/14694 and WO 97/23484, the teachings of all of which are hereby incorporated by reference in their entirety. The nitrogen of the carbamate bond of the aromatic carbamoyl ester can be substituted. Particular examples of aromatic carbamoyl esters are miotin, eserine (also referred to as physostigmine), geneserine, neostigmine, phenserine (Brossi, A., et al, *Aust. J Chem.* 49:171-181 (1996), the teachings of which are hereby incorporated by reference in their entirety), CHF2819 (Trabace, L., et al., *CNS Drug Reviews* 8:53-69 (1992), the teachings of which are hereby incorporated by reference in their entirety) and heptylphysostigmine (DeSarno, P., et al., *Neurochem. Res.* 14:971-977 (1989), the teachings of which are hereby incorporated by reference in their entirety). In one embodiment, the aromatic carbamoyl esters are known compounds, such as stigmines, that have been modified. The modification can include, for example, substitutions at the nitrogen of the carbamate bond. These compounds are collectively referred to herein as "substituted stigmines." In another embodiment, the carbamoyl ester can include an isomer or stereoisomer (e.g., d, l, dl, R, S, or RS). In all structures shown herein, it is to be understood that, whether a compound is represented as (+, −), (±), dl (DL) or (R)(S), the invention is intended to include racemic mixtures, or pure compositions of one form of the compound, e.g. "d" or "l," "R" or "S," unless otherwise specified.

Methods to prepare the carbamoyl esters of the invention, such as aromatic carbamoyl esters, are within the knowledge of one skilled in the art (see, for example, U.S. Pat. Nos. 5,665,880; 5,677,457; and WO 97/14694, the teachings of which are hereby incorporated by reference in their entirety).

In one embodiment, synthesis of aromatic carbamoyl esters can be accomplished by activation of an amine group of a compound to form an activated amine. The activated amine can be isolated and reacted with a phenol group of another compound to form the carbamoyl ester. For example, a primary amine can be converted into an isocyanate. Alternatively, amines can be converted into carbamoyl chlorides. Amines can also be activated and used in situ for the formation of the carbamoyl ester, such as by reacting an amine with activating agents that contain carbonyl chlorides (e.g. phosgene, triphosgene), by reacting the amine with activating agents that contain nitrophenyloxycarbonyl groups (e.g. bis-4-nitrophenylcarbonate, 4-nitrophenylchloroformate), or by reacting the amine with carbonyldiimidazole. The individual steps of amine activation and formation of the carbamoyl ester can be catalyzed by a variety of agents, such as acids, bases, and nucleophiles, separately or in combination.

In another embodiment, synthesis of the carbamoyl esters can be accomplished by activation of a phenol group of a compound to form an activated phenol. The activated phenol is reacted with an amine group of another compound. Activation of the phenol can be performed in a variety of ways, such as by reacting the phenol with activating agents that contain carbonyl chlorides (e.g., phosgene, triphosgene), by reacting the phenol with activating agents that contain nitrophenyloxycarbonyl groups (e.g., bis-4-nitophenylcarbonate, 4-nitrophenylchloroformate), or by reacting the phenol with carbonyldiimidazole. The individual steps of phenol activation and formation of the carbamoyl ester can be catalyzed by a variety of agents, such as acids, bases, and nucleophiles, separately or in combination.

The carbamoyl esters can be analyzed by well-known analytical methods, including NMR.

Carbamoyl esters can be synthesized, for example, by reaction of the phenolic hydroxyl group in eseroline (16 g) with carbonyldiimidazole (CDI) (15.1 g) (94 mmol) in 100 mL ethylacetate followed by addition of 14.8 mL acetic acid and 90 mmol of the amine resulted in formation of the aromatic carbamoyl ester (Gao et al., *J. Heterocyclic Chem* 37:331-333 (2000), the teachings of which are hereby incorporated by reference in their entirety).

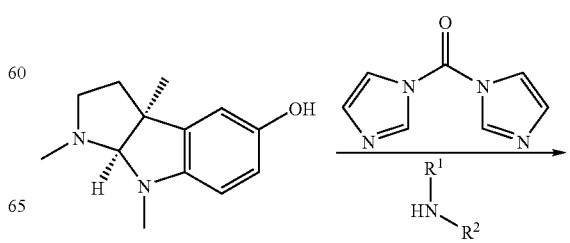

-continued

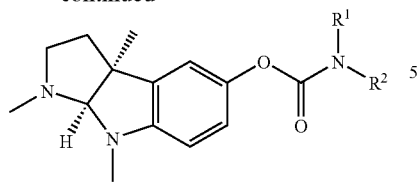

Formation of aromatic carbamoyl esters from eseroline has been described using carbamoyl chlorides (Marta, et al., *Bichimica et Biophysica Acta* 1120:262-266 (1992); Marta, et al., *Biomed Biochem Acta* 47:285-288 (1998); Marta, et al., *Life Sci.* 43:1921-1928 (1988), the teachings of which are hereby incorporated by reference in their entirety).

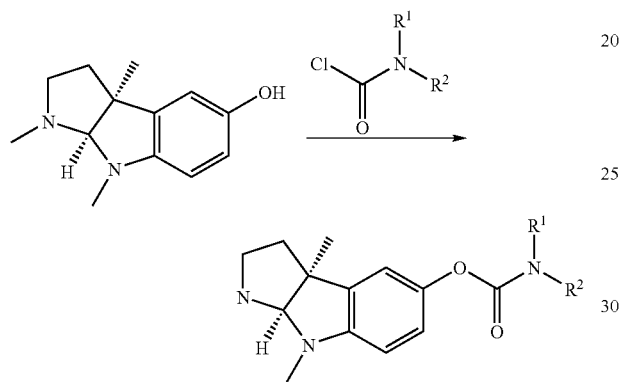

Reaction of a phenolic hydroxyl group with carbamoyl chlorides has also been described for the synthesis of aromatic carbamoyl esters (Toda, et al., *Bioorg Med Chem* 11:1935-1955 (2003), Kogen, et al., *Org Lett* 4:3359-3362 (2002), Mustazza, et al., *Eur J. Med Chem* 37:91-109 (2002) and Sterling, et al., *J Med Chem* 45:5260-5279 (2002), the teachings of all of which are hereby incorporated by referenced in their entirety).

Physovenine analogs were prepared by reaction of physovenol with alkylisocyanates in dry diethyl ether in the presence of a trace of sodium (Yu, et al., *Helvetica Chimica Acta*, 74:761-766 (1991), the teachings of which are hereby incorporated by reference in their entirety).

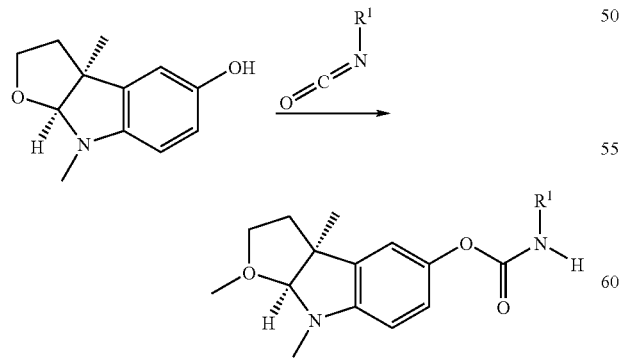

Phenserine and its analogs have been prepared by reaction of eseroline with an isocyanate (U.S. Pat. No. 6,495,700, the teachings of which are hereby incorporated by reference in their entirety), by reaction in dimethoxyethane under an argon atmosphere in the presence of catalytic amounts of n-butyllithium in hexanes.

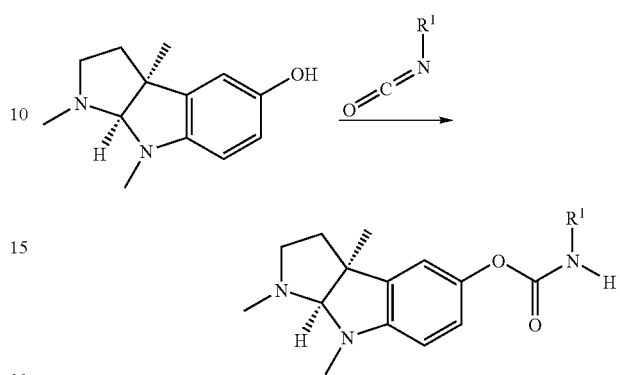

Isocyanates were also employed by Mustazza, et al., *Eur J Med Chem* 37:91-109 (2002) and Yuv et al., *J Med Chem* 44:4062-4071 (2001), the teachings of all of which are hereby incorporated by reference in their entirety.

In yet another embodiment, the aromatic carbamoyl ester is selected from the group consisting of:

III

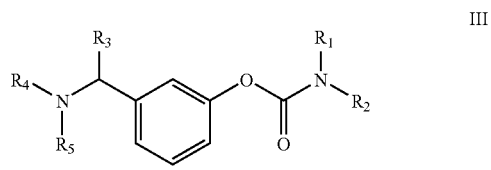

IV

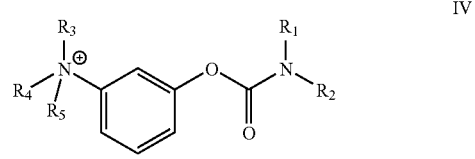

V

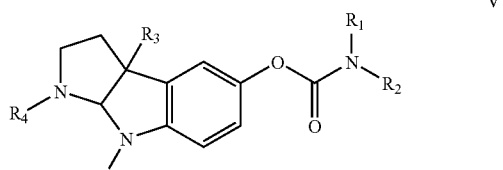

VI

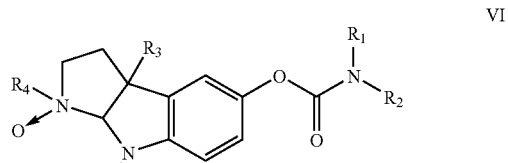

VII

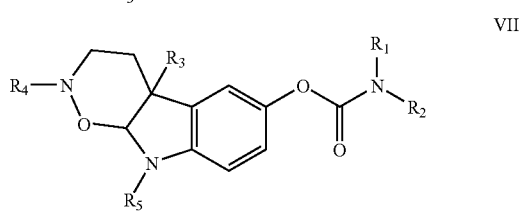

-continued

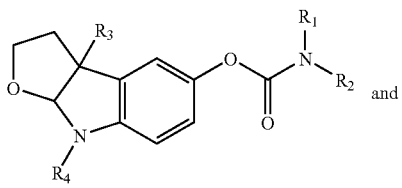
VIII and

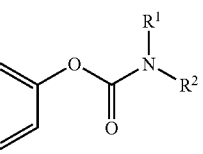
IX wherein R₃, R₄ and R₅ are each, independently or in combination, selected from the group consisting of a hydrogen, an unsubstituted alkyl, a substituted alkyl, an unsubstituted aralkyl, a substituted aralkyl, an unsubstituted heteroalkyl, a substituted heteroalkyl, an unsubstituted heteroaralkyl, a substituted heteroaralkyl, an unsubstituted aryl, a substituted aryl, an unsubstituted heteroaryl, a substituted heteroaryl, an unsubstituted cycloalkyl, a substituted cycloalkyl, an unsubstituted heterocycloalkyl and a substituted heterocycloalkyl.

In still another embodiment, the carbamoyl ester of the invention is selected from the group consisting of:

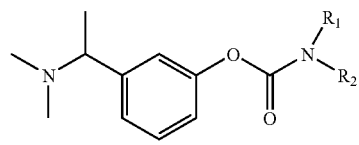
X

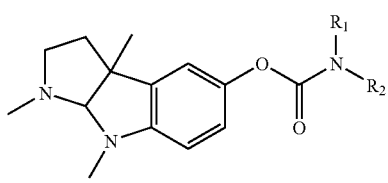
XI

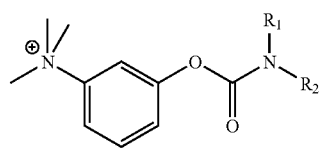
XII

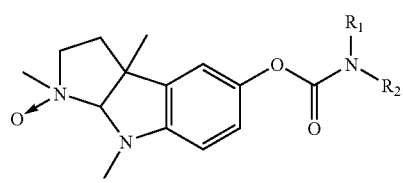
XIII

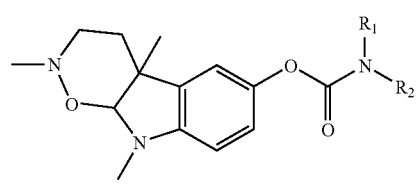
XIV

-continued

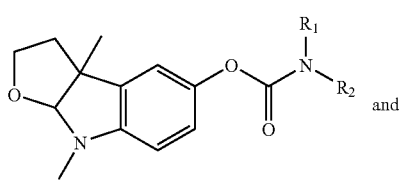
XV and

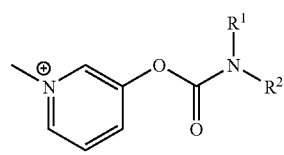
XVI

In an additional embodiment, the carbamoyl ester is selected from the group consisting of:

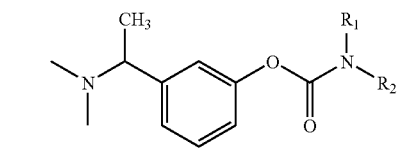

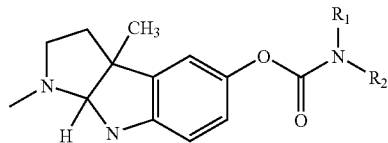

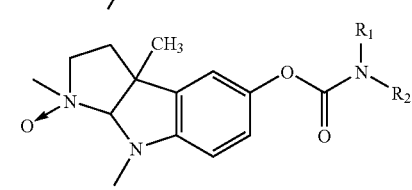

and

[additional structure]

In a further embodiment, the carbamoyl ester is selected from the group consisting of:

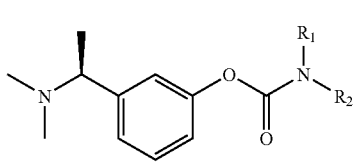
XVII

-continued

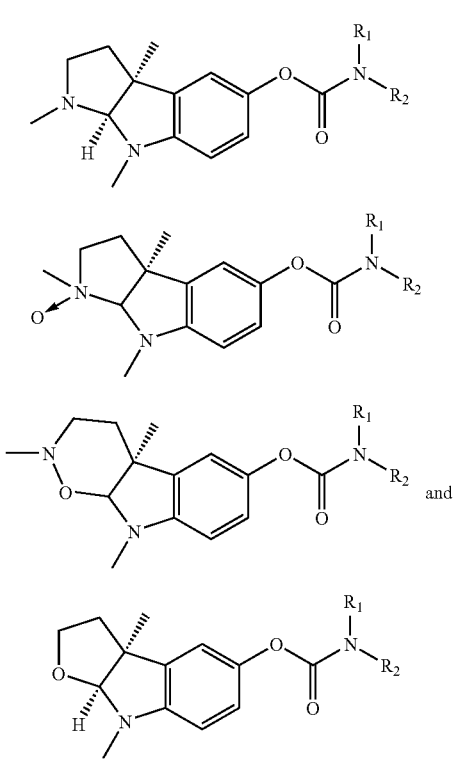

In one embodiment, the pharmacologically active agent is a memory-facilitating agent. In another embodiment, the pharmacologically active agent is a cognition-facilitating agent.

The term "memory-facilitating agent," as used herein, refers to a compound that promotes memory in an individual, prevents or minimizes a decline in memory in an individual or participates in biological processes which are involved in memory function. In a preferred embodiment, the memory-facilitating agent is an amphetamine compound. The amphetamine compound can be d-amphetamine, l-amphetamine or a mixture, such as a racemic mixture, of d-amphetamine and l-amphetamine. In another preferred embodiment, the memory-facilitating agent is methamphetamine. The methamphetamine compound can be d-methamphetamine, l-methamphetamine or a mixture, such as a racemic mixture, of d-methamphetamine and l-methamphetamine.

The memory processes which can be facilitated by the memory-facilitating agent can be memory consolidation, the process of storing new information in long term memory ("Neuroscience: Exploring The Brain," Bear, M. F. et al., Williams & Wilkins, Baltimore, Md., Ch. 19, pp. 517-545 (1996); McGaugh, J. L. Science 287: 248-251 (2000), the teachings of which are hereby incorporated by reference in their entirety); short-term memory (also referred to as "working memory"), the process whereby newly acquired information is maintained for short periods of time and the newly acquired information is made available for further information processing ("Neuroscience: Exploring The Brain," Bear, M. F. et al., Williams & Wilkins, Baltimore, Md., Ch. 19, pp. 517-545 (1996); McGaugh, J. L. Science 287: 248-251 (2000); Becker, J. T., et al., Brain and Cognition 41:1-8 (1999), the teachings of which are hereby incorporated by reference in their entirety); declarative memory, which is the memory of facts and events ("Neuroscience: Exploring The Brain," Bear, M. F. et al., Williams & Wilkins, Baltimore, Md., Ch. 19, pp. 517-545 (1996); McGaugh, J. L. Science 287: 248-251 (2000); Tulving, E., et al., Science 247: 301-306 (1990); Squire, L. R., et al., Proc. Natl. Acad. Sci. 93: 13515-13522 (1996), the teachings of which are hereby incorporated by reference in their entirety); procedural memory (also referred to as "tacit knowledge" or "implicit knowledge"), which is the memory for skills or behavior ("Neuroscience: Exploring The Brain," Bear, M. F. et al., Williams & Wilkins, Baltimore, Md., Ch. 19, pp. 517-545 (1996); McGaugh, J. L. Science 287: 248-251 (2000), the teachings of which are hereby incorporated by reference in their entirety); or attention, acquisition, retrieval or retention. One of skill in the art would be capable of identifying and evaluating the agents which would be suitable as memory-facilitating agents.

In another embodiment, the pharmacologically active agent is a cognition-facilitating agent. The term "cognition-facilitating agent," as used herein, refers to a compound that promotes activities associated with thinking, learning and acquiring knowledge in an individual, prevents or minimizes a decline in thinking, learning and acquiring knowledge in an individual or participates in biological processes which are involved in thinking, learning and acquiring knowledge. The decline in thinking, learning and acquired knowledge (a cognitive disorder) can be a consequence of or associated with another disease (e.g., Alzheimer's disease) or condition of the central, or peripheral or autonomic nervous system. The cognitive process that can be facilitated by the cognition-facilitating agent can be assessed by behavioral criteria and behavioral assays which, in turn, can further define where, in the learning, thinking, and acquiring knowledge process, the cognition-facilitating agents are acting. One of skill in the art would be capable of identifying and evaluating agents that would be suitable as cognition-facilitating agents.

In a preferred embodiment, the cognitive-facilitating agent is an amphetamine compound. The amphetamine compound can be amphetamine or methamphetamine. Amphetamine can be d-amphetamine, l-amphetamine, a racemic mixture of d-amphetamine and l-amphetamine or any mixture of d- and l-amphetamine. In another preferred embodiment, the cognitive-facilitating agent is methamphetamine. The methamphetamine can be d-methamphetamine, l-methamphetamine, a racemic mixture of d-methamphetamine and l-methamphetamine or any mixture of d- and l-methamphetamine.

The term "amphetamine," such as is used when referring to "l-amphetamine" and "d-amphetamine," means a compound represented by Formula XXII, including prodrugs and other structural and functional derivatives thereof wherein the primary amine group is available for substitution. In a preferred embodiment, the amphetamine is the compound represented by Formula XXII:

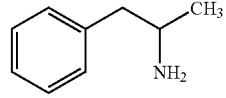

XXII

The dextro enantiomer of amphetamine is referred to as the d, (+), D or S isomer and is represented by the following structural formula:

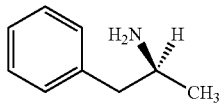

XXIII

The levo enantiomer of amphetamine can be referred to as the l, (−), L or R and is represented by the following structural formula:

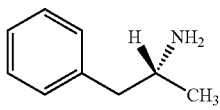

XXIV

Racemic mixtures of d-amphetamine and l-amphetamine are referred to as dl, (+, −), (±), or DL or (R)(S).

An (R)-(−)-amphetamine employed in the methods of the invention is represented by the structural formula:

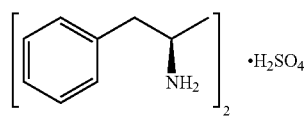

XXV

Formula XXV is also referred to as levo-amphetamine sulfate or l-amphetamine sulfate. Formula XXV has the molecular formula $C_{18}H_{28}N_2O_4S$ and a molecular weight of 368.50. The IUPAC chemical name of Formula XXV is (−)-1-methyl-2-phenylethylamine sulfate (2:1) and the CAS chemical name (−)-α-methylphenethylamine sulfate (2:1).

The term "methamphetamine," such as is used when referring to "l-methamphetamine" and "d-methamphetamine," means a compound represented by Formula XXVI:

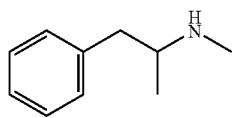

XXVI

The (R)-(−)-methamphetamine can be represented by the structural formula:

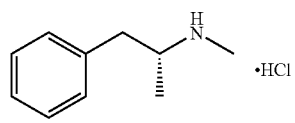

XXVII

Formula XXVII is also referred to levo-methamphetamine HCl, l-methamphetamine HCl or levomethamphetamine HCl. Formula XXVII has the molecular formula $C_{10}H_{16}NCl$.

In still another embodiment, the (R)-(−)-methamphetamine can be represented by the structural formula:

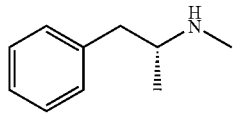

XXVIII

Formula XXVIII is also referred to levo-methamphetamine, levo-desoxyephedrine, l-desoxyephedrine or levmetamfetamine. Formula XXVIII has the molecular formula $C_{10}H_{15}N$ and a molecular weight of 149.24.

In a further embodiment, the pharmacologically active agent is at least one member selected from the group consisting of a cholinergic (also referred to as ACh) agent, an adrenergic (also referred to as epinephrine) agent, a noradrenergic (also referred to as norepinephrine) agent, a dopaminergic agent, a serotonergic (also referred to as 5-hydroxytryptamine) agent, a glutamatergic agent, a GABAergic (gamma-aminobutyric acid) agent, a histaminergic agent (e.g., HTMT, amthamine, immepip, and alpha-methylhistamine (Tocris, Ellisville, Mo.)), a mono-amine oxidase inhibitor, a catechol-O-methyl transferase (COMT) inhibitor, a beta secretase inhibitor, a gamma secretase inhibitor, a potassium channel blocker, a calcium channel blocker (e.g., nimodipine), an adenosine receptor modulator, a cannabinoid receptor modulator (e.g., virodhamine), a nootropic (i.e., cognition enhancing agent) (e.g., safinamide, minaprine, indeloxazine), a neuropeptide pathway modulator, a neurotrophic (i.e., an agent that induces neuronal cell growth), phosphodiesterase (PDE) IV inhibitor, a phosphatase/calcineurin inhibitor, a carbonic anhydrase inhibitor (e.g., brinzolamide, dorzolamide), a receptor trafficking regulator, a trace amine receptor modulator, a sigma receptor modulator, imidazoline receptor modulator, a sodium/calcium exchange blocker (also referred to as a $Na^+Ca^{+2}$ exchanger or NCX), ACE (Angiotensen Converting Enzyme) inhibitors, antioxidants and NSAIDs (Non-Steriodal Anti-Inflammatory Drugs).

The pharmacologically active agent can also be a trace amine neurotransmitter, such as phenylethylamine, octopamine, tyramine, and tryptamine. Phenylethylamine is also referred to as a natural amphetamine (Janssen, P. A. J., et. al., *Int. J. Neuropsychopharmacol*. 2:229-240 (1999), the teachings of which are hereby incorporated by reference in their entirety). Phenylethylamine is deaminated by monoamine oxidases (Yang, H.-Y. T., et al., *J. Pharmacol. Exp. Ther.*, 187:365-371 (1973), the teachings of which are hereby incorporated by reference in their entirety). A carbamoyl ester which becomes, upon hydrolysis, e.g., by reaction with a cholinesterase, phenylethylamine can be less susceptible to initial monoamine oxidation, thereby facilitating the delivery of phenylethylamine into the nervous system of an individual.

An "agent," as used herein, refers to a compound that can produce a physical, chemical or biological effect that can be stimulatory (e.g., an activating agent) or inhibitory (e.g., a blocking agent). Agents that are stimulatory can be agonists. Agents that are inhibitory can be antagonists or inverse agonists. Inverse agonists are compounds or molecules that down-regulate receptor activated activity thereby acting in a manner that is the opposite of an agonist to the receptor. Thus, exposure or administration of an inverse agonist can result in a diminished response compared to exposure or administration of an agonist.

A cholinergic agent can be, for example, a compound that stimulates the action of ACh thereby mediating ACh-mediated cell signaling between two cells (a cholinergic agonist).

Stimulation can be, for example, a result of facilitating binding of ACh to a cell surface receptor, interference with degradation of ACh, stimulation of release of ACh, stimulation of synthesis of ACh, activation of second messengers (e.g., phospholipase C, inositol 1,4,5-triphosphate, protein kinase C, protein kinase A) that mediate ACh cell signaling, alteration of ion (e.g., sodium, potassium) channels in target cells. An agent can also inhibit or prevent any one or more of these effects (e.g., a cholinergic antagonist).

The carbamoyl ester of the invention can become a pharmacologically active agent which can specifically affect the two ACh receptor subtypes, muscarinic cholinergic receptors and nicotinic cholinergic receptors, thereby targeting a particular receptor subtype that mediates a particular biological process. In one embodiment, the cholinergic agent is selected from the group consisting of a muscarinic cholinergic receptor agonist, (Cutler, N. R., et al., *CNS Drugs* 3:467-481 (1995); Korczyn, A. D., *Drugs* 9: 2259-2267 (2000), the teachings of all of which are hereby incorporated by referenced in their entirety), a muscarinic cholinergic receptor antagonist, a nicotinic cholinergic receptor agonist, a nicotinic cholinergic receptor antagonist, an acetylcholinesterase inhibitor, a cholinergic antagonist, an allosteric modulator of a cholinergic receptor and an open channel blocker.

A muscarinic cholinergic receptor agonist or antagonist can mediate effects in a variety of tissues, including smooth muscle, cardiac muscle, exocrine glands and the nervous system of individuals. A nicotinic cholinergic receptor agonist or antagonist can also mediate effects by altering the biological, physical or chemical components of ganglia in the autonomic nervous system, at neuromuscular junctions of the peripheral or autonomic nervous system and in the central nervous system.

In another embodiment, hydrolysis of the carbamoyl ester, by reaction with a cholinesterase, causes formation of a cholinergic agonist selected from the group consisting of RJR2403 (Methyl-(4-pyridin-3-yl-but-3-enyl)-amine) (also referred to as TC2403), A85380 (3-(Azetidin-2-ylmethoxy)-pyridine), anatoxin A, epibatidine and anabasine (Tocris, Ellisville, Mo.); and TC1734 ([4-(5-Isopropoxy-pyridin-3-yl)-1-methyl-but-3-enyl]-methyl-amine) (Obinu, M. C. et al., *Progress in Neuropsychopharmacol. & Biol. Psychiatry* 26:913-918 (2002); Obinu, M. C. et al., *Internatl. J Neuropyschopharamology* 3: Suppl 1 (S361) (2003); Lipiello, P. M. et al., *Soc. Neurosci. Abstr* 24: 88 (Part 1) (1998); Gatto, G., et al., *CNS Drug Reviews*, 10:147-166 (2004)).

In an additional embodiment, the hydrolysis of the carbamoyl ester, by a cholinesterase, causes a formation of an adrenergic agent selected from the group consisting of an alpha (e.g., $\alpha_1$, $\alpha_2$) receptor agonist, a beta (e.g., $\beta_1$, $\beta_2$, $\beta_3$) receptor agonist, an alpha receptor antagonist and a beta receptor antagonist. The adrenergic agents can modulate neurons and receptors involved in the actions of adrenaline and any neuronal or hormonal functions which are mediated or affected by adrenaline. Since noradrenaline can also act through alpha and beta receptors, the pharmacologically active agents can affect biological, chemical or physical processes associated with noradrenaline. In a preferred embodiment, the adrenergic agent is a primary or secondary amine. Adrenergic agents include at least one member of the group selected from the group consisting of oxymetazoline, cirazoline, clonidine, A61603, agmatine, atenolol, betaxolol, bisoprolol, BRL 37344, BRL44408, cimaterol, dobutamine, efaroxan, formoterol, HEAT, ICI 118551, IC189406, ICL215001, idazoxan, pindolol, practolol, procaterol, pronethalol, propanolol, RX821002, SB206606, SR59230A, sotalol, WB4101, xamoterol, ZD7114, efaroxan and clenbuterol (Tocris, Ellisville, Mo.); and adrenaline, brimonidine, dipifevrin, and metipranolol.

In yet another embodiment, hydrolysis of the carbamoyl ester, e.g., by reaction with a cholinesterase, causes formation of a noradrenergic agent selected from the group consisting of a norepinephrine re-uptake inhibitor and a norepinephrine releasing agent. The norepinephrine re-uptake inhibitor can prevent or minimize the removal of norepinephrine from a synapse, thereby increasing the amount of norepinephrine in the synapse. Prevention of norepinephrine removal can be active (e.g., by blocking a cellular process involved in re-uptake) or passive (e.g., by stabilizing norepinephrine). The norepinephrine agent can result in release of norepinephrine from a cell (e.g., a nerve cell, a secretory cell, an epithelial cell). Other compounds referred to herein as "re-uptake inhibitors" and "releasing agents," act in a similar manner, but specific for the particular pharmacologically active agent, such as a neurotransmitter. The norepinephrine re-uptake inhibitor can be, for example, viloxazine, and/or nisoxetine (Tocris, Ellisville, Mo.); maprotiline, atomoxetine, MCI225 (4-(2-Fluoro-phenyl)-6-methyl-2-piperazin-1-yl-thieno[2,3-d]pyrimidine hydrochloride), oxaprotiline, reboxetine, talopram, talsupram, and thionisoxetine; and amoxapine, desipramine, methylphenidate, nomifensine, nortriptyiline, and protriptyline (Sigma Chemical Co., St., Louis, Mo.).

In a further embodiment, hydrolysis of the carbamoyl ester, e.g., by reaction with a cholinesterase, causes formation of a serotonergic agent selected from the group consisting of a serotonergic antagonist, a serotonergic agonist, a serotonergic re-uptake inhibitor and a serotonin releasing agent. The serotonergic agents can, for example, affect neurotransmission or hormone release from endocrine glands. Serotonergic agents can include at least one member selected from the group consisting of pindolol, quipazin, fluoxetine, anpirtoline, N-(4-bromobenzyl)-5-methoxytryptamine, BW 723C86, 5-carboxamidotryptamine, m-CPP, N-desmethylclozapine, desmethylcitalopram, isamoltane, L-694247, MDL 72832, MDL 73005EF, alpha-methyl-5-hydroxytryptamine, 2-methyl-5-hydroxytryptamine, mianserin, MK212, 5-nonyloxytryptamine, 6-nitroquipazine, norfluoxetine, paroxetine, RS 67333, RS 67506, RS 23597-190, RS 39604, RU 24969, sertraline, desmethylsertraline, SR 57227, TFMPP, and fluvoxamine (Tocris, Ellisville, Mo.); and MMAI, RS17017 (1-(4-Amino-5-chloro-2-methoxy-phenyl)-5-piperidin-1-yl-pentan-1-one hydrochloride), RS 66331, SB271046 (5-Chloro-3-methyl-benzo[b]thiophene-2-sulfonic acid (4-methoxy-3-piperazin-1-yl-phenyl)-amide), SB 399885, and SL65.0155 ((5-(8-Amino-7-chloro-2,3-dihydro-benzo[1,4]dioxin-5-yl)-3-(1-phenethyl-piperidin-4-yl)-3H-[1,3,4]oxadiazol-2-one hydrochloride).

In yet another embodiment, hydrolysis of the carbamoyl ester, e.g., by reaction with a cholinesterase, causes formation of a glutamatergic agent selected from the group consisting of an NMDA (N-methyl-D-aspartate) receptor agonist, an NMDA receptor antagonist, an NMDA glycine site agonist, an NMDA glycine site antagonist, an AMPA (α-amino-3-hydroxy-5-methyl-4-isoxazole proprionate) receptor agonist and an AMPA receptor antagonist, a kainate receptor agonist and a kainate receptor antagonist. Additionally, or alternatively, the glutamatergic agent can include an NMDA ion-channel modulator, an NMDA polyamine site agonist, an NMDA polyamine site antagonist, an AMPA/kainate agonist, an AMPA/kainate antagonist, a Group I metabotropic glutamate receptor agonist, a Group I metabotropic glutamate receptor antagonist, a Group II metabotropic glutamate receptor agonist, a Group II metabotropic glutamate receptor antagonist, a Group III metabotropic glutamate receptor agonist, a Group III metabotropic glutamate receptor antagonist, a quisqualate-sensitive AP6 site agonist, a quisqualate-sensitive AP6 site antagonist and an excitatory amino acid uptake inhibitor. Examples of metabotropic glutamate receptor compounds include 2-methyl-6-(phenylethynyl)-pyridine (MPEP), trans-ACPD, ACPT-I, ACPT-II, ACPT-III, tADA, AIDA, AP3, AP4, AP5, AP6, (2R,4R)-APDC, APICA, 3-carboxy-4-hydroxyphenylglycine, 4-carboxy-3-hydroxyphenylglycine, 4-carboxyphenylglycine, L-CCG-I, CHPG, CPPG, 1-cysteinesulfinic acid, DCG IV, 3,4-DCPG, 3,5-DHPG, E4CPG, EGLU, L-3'F2CCG-I, 1-glutamic acid, homoAMPA, 3-hydroxyphenylglycine, ibotenic acid, LY307452, LY341495, LY367385, MAP4, MCCG, MCPG, MPPG, MSOP, MSPG, MTPG, alpha-methyl-3-carboxymethylphenylglycine, o-phospho-l-serine, PPG, quisqualic acid, s-sulfo-l-cysteine, UBP1112, and spaglumic acid (Tocris, Ellisville, Mo.). Other glutamate receptor compounds include lamotrigine, riluzole, and salsolinol-l-carboxylic acid (Tocris, Ellisville, Mo.).

NMDA agents can include aspartic acid, D-cycloserine, ACBC, trans-ACBD, cis-ACPD, AP4, AP5, AP7, aspartic aicd, 4-carboxyphenylglycine, CGP37849, CGP39551, CGS19755, CGP78608, chlorpheg, CPP, L-cysteinesulfinic acid, glutamic acid, glycine, HA-996, N-(4-hydroxyphenylacetyl)spermine, N-(4-hydroxyphenylpropanol)spermine, ibotenic acid, L689560, LY 235959, MK 801, NMDA, SDZ 220-040, SDZ 220-581, d-serine, (tetrazol-5-yl)glycine, memantine, spermine and spermidine (Tocris, Ellisville, Mo.); and amantadine (Sigma Chemical Co., St. Louis, Mo.). AMPA/kainate agents can include L-quisqualic acid, domoic acid, kainic acid, AMPA, ATPA, CFM-2, (S)-CPW 399, 5-fluorowillardiine, 5-iodowillardiine, willardiine, GAMS, GYKI, 52466, IDRA 21, SYM 2081, and SYM 2206 (Tocris, Ellisville, Mo.).

An excitatory amino acid uptake inhibitor can be dihydrokainic acid, cis-ACBD, L-CCG-II, chlorpheg, dihydrokainic acid, threo-3-hydroxyaspartic acid, threo-3-methylglutamic acid, MPDC, trans-2,4-PDC, SYM2081, and TBOA (Tocris, Ellisville, Mo.).

The NMDA receptor antagonist can be memantine (Tocris, Ellisville, Mo.) (Parsons, C. G., et al., *Neuropharmacol.*, 38:735-767 (1999), the teachings of which are hereby incorporated by reference in their entirety). The NMDA glycine receptor agonist can be D-cycloserine (Sigma Chemical Company, St. Louis, Mo.) (Land, C., et al., *Neurobiol. Learning Mem.*, 72:158-168 (1999), the teachings of which are hereby incorporated by reference in their entirety).

In a further embodiment, hydrolysis of the carbamoyl ester, e.g., by reaction with a cholinesterase, causes formation of a GABAergic agent which is selected from the group consisting of a GABAergic receptor antagonist, a GABAergic receptor agonist, a benzodiazepine site agonist, a benzodiazepine site antagonist, a benzodiazepine site inverse agonist and a GABA uptake inhibitor. The GABAergic can include, for example, muscimol, baclofen, saclofen, 1-amino-5-bromouracil, CACA, CGP35348 ((3-piperazin-Amino-propyl)-diethoxymethyl-phosphinic acid), CGP46381 ((3-Amino-propyl)-cyclohexylmethyl-phosphinic acid), CGP 52432, CGP 54626, CGP 55845, GABA, GBLD 345, 2-hydroxysaclofen, isoguvacine, phaclofen, SB 205384, SCH 50911, SKF 97541, TACA THIP, TPMPA, and tracazolate (Tocris, Ellisville, Mo.); SR 95531 and SGS742 ((3-Amino-propyl)-butyl-phosphinic acid) (Kerr, D. I. B. et al., *J. Ong. Pharmac. Ther.* 67: 187-246 (1995); Froestl, W., et al., *Biochem. Pharmacol.*, 68:1479-1487 (2004)).

In another embodiment, hydrolysis of the carbamoyl ester, e.g., by reaction with a cholinesterase, causes formation of a dopaminergic agent selected from the group consisting of a dopaminergic antagonist, dopaminergic agonist, a dopaminergic re-uptake inhibitor, a dopaminergic releasing agent, dopamine and L-DOPA (levodopa) (3,4-dihydroxyphenylalanine, 3-hydroxytyrosine). Since dopamine is an intermediate in the synthesis of noradrenaline, adrenaline and melanin, any agent which affects dopamine can produce a physical, chemical or biological effect in biological processes associated with or mediated by noradrenaline, adrenaline and melanin. The dopaminergic agent can affect dopamine as a hormone or dopamine as a neurotransmitter. The dopaminergic agent can include, for example, dihydrexidine, A68930 (1-Aminomethyl-3-phenyl-isochroman-5,6-diol), SKF 38393, AJ 76, 4-phenyl-1,2,3,4-tetrahydroisoquinoline, and rimcazole (Tocris, Ellisville, Mo.); and A77636 (3-Adamantan-1-yl-1-aminomethyl-isochroman-5,6-diol), adrogolide, and SKF81297 (6-Chloro-1-phenyl-2,3,4,5-tetrahydro-1H-benzo[d]azepine-7,8-diol); pergolide (Sigma Chemical Company, St., Louis, Mo.) and pramipexole (also referred to as MIRAPEX™).

A "modulator," as used herein, refers to a compound that regulates, adjusts or adapts a biological pathway or receptor-mediated signal transduction pathway. The modulators can stimulate or inhibit a biological pathway or receptor-mediated signal transduction pathway. For example, an adenosine receptor modulator can increase the capacity of adenosine to bind the receptor, decrease the capacity of adenosine to bind the receptor, directly bind to the receptor (e.g., an agonist or inverse agonist) and have an effect or otherwise interact with the receptor to regulate, adjust or adapt a biological pathway associated with an adenosine receptor mediated signal transduction pathway.

In another embodiment, hydrolysis of the carbamoyl ester, e.g., by reaction with a cholinesterase, causes formation of at least one member selected from the group consisting of a mono-amine oxidase inhibitor, COMT inhibitor, beta secretase inhibitor or a gamma secretase inhibitor.

An inhibitor prevents an enzyme from participating in a biological process or diminishes the activity of the enzyme in the biological process. For example, a beta secretase inhibitor or a gamma secretase inhibitor can prevent the formation of beta-amyloid protein from amyloid precursor protein in the brain of a human. Accumulation of beta amyloid protein is associated with Alzheimer's disease in humans. Thus, a decrease in beta amyloid protein can ameliorate, prevent or diminish the onset or progression of Alzheimer's disease.

In a particular embodiment, the mono-amine oxidase inhibitor is at least one member selected from the group consisting of desmethylselegline (Heinonen, E. H., et al., *J. Clin. Pharmacol.* 37:602-609 (1997), the teachings of which are hereby incorporated by reference in its entirety), rasagiline (Kupsch, A., *Curr. Opin. Investig. Drugs* 3:794-979 (2002), the teachings of which are hereby incorporated by reference in its entirety), 1-(benzofuran-2-yl)-2-propylaminopentane, 5-benzyloxy-2-indolylmethylamine, lazabemide, CHF3381 (2-(Indan-2-ylamino)-acetamide), milacemide, mofegeline, brofaromine, Ro-41-1049, RS-1636; and bifemelane, and tetrindol (Tocris, Ellisville, Mo.).

In another embodiment, hydrolysis of the carbamoyl ester, e.g., by reaction with a cholinesterase, causes formation of a potassium ion channel blocker, such as 4-amino pyridine. Since the selective permeability of a potassium channel is important to the resting membrane potential of a cell, blocking of a potassium ion channel can potentiate or prolong depolarization of a membrane, thereby augmenting cellular signaling, for example, of neurons.

The pharmacologically active agents can affect cells of the central nervous system, peripheral nervous system, autonomic nervous system and other tissues (e.g., smooth muscle, cardiac muscle, skeletal muscle) and organs (e.g., endocrine glands, exocrine glands).

In one embodiment, the pharmacologically active agent can be an exogenous agent (originating or produced outside of the individual). In another embodiment, the pharmacologically active agent can be an endogenous (originating or produced inside the individual) agent that has been purified from a biological source obtained from an individual.

The physical, chemical or biological effect that can be stimulated or inhibited by the carbamoyl esters of the invention and the pharmacologically active agents of the invention can be between two or more cells. In one embodiment, the two or more cells are two or more nerve cells (pre-synaptic neuron, post-synaptic neuron). The nerve cells can be in the central nervous system, the peripheral nervous system or the autonomic nervous system. In another embodiment, the two or more cells can be at least one muscle cell (smooth muscle, skeletal muscle, cardiac muscle) and at least one nerve cell (pre-synaptic neuron, post-synaptic neuron). In still another embodiment, the two or more cells can be at least one nerve cell and at least one non-neuronal cell (e.g., a secretory cell of the adrenal medulla, a cell of an exocrine gland or endocrine gland, an epithelial cell of an organ or tissue). The two or more cells can be cells in vitro (e.g., cell culture) or cells in vivo (e.g., in an individual).

The pharmacologically active agent can be a nootropic agent (i.e., cognition enhancing agent), a neurotrophic agent (i.e., an agent which induces neuronal cell growth) and/or a neuroprotective agent.

In still another embodiment, the invention is a method of treating an individual. The method includes administering to the individual a carbamoyl ester. The carbamoyl ester inhibits a cholinesterase and includes an amine group that, upon hydrolysis, e.g., by reaction with the cholinesterase, becomes at least a component of a pharmacologically active agent that treats the individual for a condition of the individual.

The pharmacologically active agent released by the carbomyl ester is at least one member selected from the group consisting of a cholinergic agent, an adrenergic agent, a noradrenergic agent, a dopaminergic agent, a serotonergic agent, a glutamatergic agent, a GABAergic agent, a histaminergic agent, a mono-amine oxidase inhibitor, a COMT inhibitor, a beta secretase inhibitor, a gamma secretase inhibitor, a potassium channel blocker, a calcium channel blocker, an adenosine receptor modulator, a cannabinoid receptor modulator, a nootropic, a neuropeptide pathway modulator, a neurotrophic, a PDE IV inhibitor, a phosphatase/calcineurin inhibitor, a receptor trafficking regulator and a trace amine receptor modulator.

The carbamoyl ester of the invention can inhibit cholinesterase activity, which can be expressed as an IC50. The term "IC50," as used herein, refers to the concentration of a drug, compound, molecule or carbamoyl ester that inhibits an activity or effect by 50%, e.g., by reducing the frequency of a condition, such as memory or cognitive loss by 50%; by reducing binding of a competitor molecule to a protein (e.g., a receptor) by 50%; or by reducing the level of an activity (e.g., cholinesterase activity) by 50%.

As used herein, an "individual" is any mammal. A mammal can be a rodent (such as a rat, mouse or guinea pig), domesticated animal (such as a dog or cat), ruminant animal (such as a horse or a cow) or a primate (such as a monkey or a human). In a preferred embodiment, the individual is a human.

The condition of the individual that is treated by the pharmacologically active agent is at least one condition selected from the group consisting of a central nervous system condition, a peripheral nervous system condition and an autonomic nervous system condition.

In a particular embodiment, the individual treated with the carbamoyl ester has a central nervous system condition. A "central nervous system condition," as used herein, refers to any illness or ailment that affects the brain or spinal cord of the individual. Central nervous system conditions treated with the carbamoyl esters of the invention, can, for example, be a consequence of a genetic disease, environmental exposure to a compound or secondary to a primary illness or disease. The central nervous system condition can be characterized by or a consequence of inadequate neurotransmitter release, synthesis, processing, re-uptake or cell signaling. The central nervous system condition can additionally, or alternatively, be characterized by or a consequence of failed or inadequate neuronal transmission due to disruptions in ion channels.

In a particular embodiment, the central nervous system condition is treated with a carbamoyl ester that includes a substituted stigmine. The carbamoyl esters of the invention can be used to treat conditions including depression, anxiety and mental retardation. Central nervous system conditions in an individual treated by the carbamoyl esters of the invention can be Parkinson's disease, a memory impairment and a cognitive impairment.

The memory impairments can be in a human individual. Memory impairments that can be treated by the carbamoyl esters of the invention include Alzheimer's disease, age-associated memory loss, an impairment in memory consolidation, an impairment in short term memory, mild cognitive impairment, an impairment in declarative memory and impairments in memory associated with or a consequence of multiple sclerosis and/or Parkinson's disease.

The memory impairment treated by the carbamoyl esters of the invention can be a consequence of exposure to a muscarinic cholinergic receptor antagonist. In one embodiment, the muscarinic cholinergic receptor antagonist is atropine. In another embodiment, the muscarinic cholinergic receptor antagonist is scopolamine. In yet another embodiment, the muscarinic cholinergic receptor antagonist is homatropine.

A muscarinic cholinergic receptor antagonist includes any substance which blocks, diminishes, attenuates, inhibits, hinders, limits, decreases, reduces, restricts or interferes with the action of ACh thereby disrupting ACh-mediated cell signaling between presynaptic and postsynaptic neurons. The antagonist can, for example, oppose the action of ACh by acting in a manner which prevents ACh from binding to a muscarinic cholinergic receptor on a postsynaptic neuron, from mediating post-synaptic events following binding of ACh to a muscarinic cholinergic receptor, interfere with ACh degradation by acetylcholinesterase in the synaptic cleft or interfere with release of ACh from presynaptic neurons.

In still another embodiment, the carbamoyl esters of the invention can be used to treat a peripheral nervous system condition in an individual. The peripheral nervous system condition can, for example, be a disease or illness consequent to or associated with neurons which supply innervation to a skeletal muscle (e.g., Myasthenia Gravis). Conditions of the peripheral nervous system can be, for example, an impairment in the release of acetylcholine from neurons at the neuromuscular junction of skeletal, smooth or cardiac muscle.

The carbamoyl esters of the invention can be used to treat an autonomic nervous system condition (sympathetic nervous system, parasympathetic nervous system) in an individual. The autonomic nervous system conditions can be conditions which affect smooth muscle of viscera, glands (endocrine glands, exocrine glands), blood vessels or cardiac muscle. Autonomic nervous system conditions treated employing the carbamoyl esters of the invention can be post-operative distension and urinary retention. Conditions of the autonomic nervous system can be an impairment in a function associated with the autonomic nervous system, for example, an impairment in the release of norepinephrine from sympathetic neurons or ACh from parasympathetic neurons at a synapse with a cell (e.g., epithelial, nervous, muscle, connective tissue) in an organ, blood vessel or gland. One skilled in the art would be capable of diagnosing an individual with a central nervous system condition, peripheral nervous system condition and an autonomic nervous system condition.

In one embodiment, upon hydrolysis, e.g., with a cholinesterase, the carbamoyl ester employed to treat the individual with a condition (central nervous system, peripheral nervous system, autonomic nervous system) becomes an amphetamine compound (l-amphetamine, d-amphetamine) and/or a methamphetamine compound (d-methamphetamine, l-methamphetamine).

An "impairment in memory or cognition," as used herein, refers to a diminished capacity in memory and/or cognitive processes in the human. The cognitive and/or memory processes and impairments in cognitive and/or memory processes can be assessed or determined by established techniques. For example, memory can be assessed before, concomitantly with or after treatment of the individual with the carbamoyl esters of the invention one or more well established tests known to one of skill in the art. Such tests include the Passive Avoidance Testing (Principles of Neuropsychopharmacology), R. S. Feldman, et al., Sinauer Assoc., Inc., Sunderland, Mass. (1997), the teachings of all of which are incorporated by reference in their entirety); Rey Auditory Verbal Learning Test (RAVLT); a Wechsler Memory Scale; Wechsler Memory Scale-Revised (Wechsler, D., Wechsler Memory Scale-Revised Manual, NY, N.Y., The Psychological Corp. (1987)); California Verbal Learning Test-Second Edition (Delis, D. C., et al., The Californian Verbal Learning Test, Second Edition, Adult Version, Manual, San Antonio, Tex.: The Psychological Corporation (2000)); Cognitive Drug Research (CDR) Computerized Assessment Battery-Wesnes; Buschke's Selective Reminder Test (Buschke, H., et al., *Neurology* 24: 1019-1025 (1974)); Brief Visuospatial Memory Test-Revised; and Test of Everyday Attention (Perry, R. J., et al., *Neuropsychologia* 38: 252-271 (2000)).

In a particular embodiment, the memory of the human before, during or after administration of the carbamoyl esters of the invention is assessed or determined by a word recall test such as RAVLT.

In another embodiment, the invention described herein provides a method of treating a nervous system condition in an individual. The method includes administering to the individual a carbamoyl ester. The carbamoyl ester inhibits a cholinesterase thereby treating the nervous system condition of the individual. The carbamoyl ester includes an amine group that, upon hydrolysis, e.g., by reaction with the cholinesterase, becomes at least a component of a pharmacologically active agent that further treats the nervous system condition in the individual. The pharmacologically active agent can, for example, sustain inhibition of the cholinesterase which was inhibited by the carbamoyl ester. The pharmacologically active agent can further treat the nervous system condition, for example, by delivering a compound to a neuron or synapse, sustaining polarization of a neuron, preventing re-uptake of a neurotransmitter, stimulating or maintaining the synthesis or release of a neurotransmitter.

In a particular embodiment, administration of the carbamoyl ester treats a central nervous system condition in an individual. The carbamoyl ester inhibits acetylcholinesterase thereby treating the central nervous system condition in the individual. The carbamoyl ester includes an amine group that, upon hydrolysis, e.g., by reaction with the acetylcholinesterase, becomes at least one component of a pharmacologically active agent that further treats the central nervous system condition in the individual. The pharmacologically active agent is selected from the group consisting of an amphetamine compound and a methamphetamine compound.

A further embodiment of the invention is a method of increasing acetylcholine in an in vitro sample. The method includes administering to the in vitro sample a carbamoyl ester. The carbamoyl ester inhibits a cholinesterase, thereby increasing acetylcholine in the in vitro sample. The carbamoyl ester includes an amine group that, upon hydrolysis, e.g., by reaction with the cholinesterase, becomes at least a component of a pharmacologically active agent that further increases the acetylcholine in the in vitro sample.

The in vitro sample can be a cell-free sample or a sample containing cells. The cells employed can be mammalian cells (e.g., CHO cells), insect cells or bacterial cells. The method can be employed to assess the ability of the carbamoyl ester to inhibit cholinesterase and the pharmacologically active agent to affect biological, chemical or physical processes prior to use in an individual. The method can be packaged in a kit as an assay for screening the carbamoyl esters for cholinesterase activity and pharmacological activity of the agents the carbamoyl ester becomes upon hydrolysis.

Another embodiment of the invention is a method of increasing acetylcholine in a tissue. The method includes administering to the tissue a carbamoyl ester. The carbamoyl ester inhibits a cholinesterase, thereby increasing acetylcholine in the tissue and includes an amine group that, upon hydrolysis, e.g., by reaction with the cholinesterase, becomes at least a component of a pharmacologically active agent that further increases acetylcholine in the tissue.

The tissue can be a nervous tissue, a muscle tissue (cardiac, skeletal, smooth muscle) or a collection of any one or more of a tissue type selected from the group consisting of nervous tissue, muscle tissue, epithelial tissue and connective tissue. The tissue can be isolated (removed from the individual).

An additional embodiment of the invention is a method of increasing acetylcholine in an individual. The method includes administering to the individual a carbamoyl ester in the individual. The carbamoyl ester inhibits a cholinesterase (e.g., AchE, BuChE), thereby increasing acetylcholine. The carbamoyl ester includes an amine group that, upon hydrolysis, e.g., by reaction with the cholinesterase, becomes at least a component of a pharmacologically active agent that further increases acetylcholine in the individual.

In one embodiment, the pharmacologically active agent increases acetylcholine in the central nervous system of the individual. In another embodiment, the pharmacologically active agent increases acetylcholine in the peripheral nervous system of the individual. In yet another embodiment, the carbamoyl ester increases acetylcholine in the autonomic nervous system of the individual. Techniques to assess the increase of ACh in an in vitro sample, in a tissue and in an individual are well-known to one skilled in the art. (See, for example, Day, J. C., et al. *Methods* 23:21-39 (2001), the teachings of which are hereby incorporated by reference in its entirety).

In a preferred embodiment, the pharmacologically active agent in the methods of the invention is an amphetamine compound and/or a methamphetamine compound.

The further increase in acetylcholine can be an increase mediated in a manner similar to the increase mediated by the carbamoyl ester (inhibition of AChE) or an increase in ACh by, for example, increasing the release of ACh, increasing the synthesis of ACh or otherwise preventing the inactivation of ACh.

In a further embodiment, the invention is a method of increasing transmission between two or more neurons. The method includes exposing the neurons to a carbamoyl ester. The carbamoyl ester inhibits a cholinesterase, thereby increasing transmission between the two or more neurons. The carbamoyl ester includes an amine group that, upon hydrolysis, e.g., by reaction with the cholinesterase, becomes at least a component of a pharmacologically active agent that further increases transmission between the two or more neurons.

The further increase in transmission can be, for example, in a manner similar to the carbamoyl ester (by inhibiting cholinesterase) or by any other manner mediated by the pharmacologically active agent, such as stimulating release or synthesis of a neurotransmitter, inhibiting re-uptake of a neurotransmitter, alter ion channels of neurons.

The transmission can be increased between two or more neurons in vitro or in vivo. Techniques to determine an increase in transmission in vitro and in vivo are well known to one skilled in the art. For example, changes in depolarization of the post-synaptic neuron can be recorded by electrophysiological methods.

The carbamoyl ester can increase transmission between two or more neurons by, for example, increasing the amount of a neurotransmitter (e.g., cholinergic, adrenergic, noradrenergic, dopaminergic, serotonergic, glutamatergic, GABAergic, histaminergic) or diminishing or preventing the degradation of a neurotransmitter (e.g., by inhibiting mono-amine oxidase, COMT) in the synapse. Additionally, or alternatively, the carbamoyl ester can increase transmission between two or more neurons, by modulating a neurotransmitter receptor (e.g., adenosine receptor, cannabinoid receptor, trace amine receptor) or blocking ion channels (e.g., potassium channel, sodium channel) in the neurons. Further, the carbamoyl ester can increase transmission between two or more neurons by inhibiting PDE IV, phosphatase/calcineurin inhibitor or regulating a receptor trafficking molecule, by inhibiting a phosphodiesterase or a phosphatase or by modulating receptor trafficking molecules (e.g., BARK, arrestin, ubiquitin E3 ligase).

An increase in transmission in an individual can minimize or alleviate central or peripheral nervous system conditions, such as memory and cognitive impairments. For example, an increase in cholinergic transmission (e.g., post-synaptic) in a human individual can minimize or alleviate the symptoms associated with Alzheimer's disease. An increase in dopaminergic transmission (e.g., post-synaptic) in a human individual can minimize or alleviate the symptoms associated with Parkinson's disease. A carbamoyl ester can, upon hydrolysis with a cholinesterase, become, for example, dopamine or a dopaminergic agent which can increase transmission (pre- or post-synaptic) in the central nervous system in human individuals with Parkinson's disease, thereby providing an alternative to L-DOPA (Levodopa). The lipophilic phenyl carbamate, for example, of the carbamoyl ester can facilitate penetration of the carbamoyl ester through the blood brain barrier, thereby permitting delivery of a pharmacologically active agent, in particular, dopamine, into the central nervous system. One skilled in the art can determine, using established techniques, the effect of the pharmacologically active agent on a human individual with a central or peripheral nervous system condition.

Another embodiment of the invention is a method of treating a cholinergic deficiency in an individual. The method includes administering to the individual a carbamoyl ester. The carbamoyl ester inhibits a cholinesterase thereby treating the cholinergic deficiency in the individual. The carbamoyl ester includes an amine group that, upon hydrolysis, e.g., by reaction with the cholinesterase, becomes at least a component of a pharmacologically active agent that further treats the cholinergic deficiency in the individual. Further treatment can be, for example, by inhibition of ACHE and/or BuChE, or by increasing release or synthesis of ACh.

The cholinergic deficiency can be a nervous system deficiency. For example, the carbamoyl esters of the invention can be used to treat a human individual having Alzheimer's disease. Presynaptic neurons degenerate rapidly in Alzheimer's disease which limits the efficacy of ChE inhibition as the disease progresses (Cutler, N. R., et. al. *CNS Drugs* 3:467-481 (1995)). ChE continues to be present in the synapses of neurons in an individual with Alzheimer's disease, hydrolyzing what little ACh may be present in the synapse. Thus, the carbamoyl esters of the invention can be become a cholinergic agonist thereby ameliorating the cholinergic deficiency by increasing ACh-mediated synaptic transmission in the central nervous system of individuals suffering from Alzheimer's disease, mild cognitive impairment, age associated memory impairment, age associated memory loss, natural aging, vascular dementia, dementia with Lewis bodies and Parkinson's disease.

In an additional embodiment, the invention is a method of treating an impairment in memory in an individual. The method includes administering to the individual a carbamoyl ester. The carbamoyl ester inhibits a cholinesterase thereby treating the impairment in memory in the individual. The carbamoyl ester includes an amine group that, upon hydrolysis, e.g., by reaction with the cholinesterase, becomes at least a component of a pharmacologically active agent that further treats the impairment in memory in the individual. Further treatment of the memory can be treatment similar to the carbamoyl ester or in a manner different than the carbamoyl ester which is characteristic of the pharmacologically active agent.

The memory impairment can be a memory impairment selected from the group consisting of an impairment in memory consolidation, an impairment in long-term memory and an impairment in short-term memory. One skilled in the art would be capable of identifying an individual with a memory impairment and assessing the impairment.

In a particular embodiment, a human individual has an impairment in memory associated with a condition selected from the group consisting of Alzheimer's disease, Parkinson's disease, age-associated memory loss, mild cognitive impairment and multiple sclerosis.

In another embodiment the human individual treated with the carbamoyl esters of the invention has age-related cognitive decline.

A further embodiment of the invention is a method of delivering a pharmacologically active agent to a tissue. The method includes administering to the tissue a carbamoyl ester. The carbamoyl ester inhibits a cholinesterase and includes an amine group that, upon hydrolysis, e.g., by reaction with the cholinesterase, becomes at least a component of a pharmacologically active agent, thereby delivering the pharmacologically active agent to the tissue.

The tissue can be an in vitro tissue sample or can be a tissue in vivo (in an individual). The tissue can be muscle tissue, nervous tissue or any combination of muscle, nervous, connective or epithelial tissue. The carbamoyl ester can be employed to deliver a pharmacologically active agent to a tissue that is proximal or distal to a tissue having a cholinesterase that is inhibited by the carbamoyl ester. For example, a carbamoyl ester can be employed to deliver a pharmacologically active agent, such as a cholinergic agent, to a muscle tissue. The carbamoyl ester can bind a cholinesterase (acetylcholinesterase, butyrylcholinesterase) thereby inhibiting the activity of the cholinesterase and, upon hydrolysis (with, for example, a cholinesterase), become a cholinergic agent. The pharmacologically active agent can be delivered to a muscle cell proximate to the site of binding of the carbamoyl ester to the cholinesterse or to a muscle cell distal to the site of binding. Similarly, the carbamoyl ester can bind to a cholinesterase in a neuron of the nervous system and deliver a cholinergic agent proximal or distal to the site of binding.

The carbamoyl ester can bind to a cholinesterase and, upon hydrolysis, e.g., by reaction with the cholinesterase, deliver, for example, a dopaminergic agent, serotonergic agent, adrenergic agent, noradrenergic agent, glutamatergic agent, GABAergic agent, histaminergic agent, mono-amine oxidase inhibitor, COMT inhibitor, beta secretase inhibitor, gamma secretase inhibitor, potassium channel blocker, calcium channel blocker, adenosine receptor modulator, cannabinoid receptor modulator, nootropic, neuropeptide pathway modulator, neurotrophic, PDE IV inhibitor, phosphatase/calcineurin inhibitor, receptor trafficking regulator or trace amine receptor modulator to a neuron proximate or distal to the site of binding of the carbamoyl ester. Thus, the carbamoyl esters of the invention provide a method of delivering a pharmacologically active agent to the central nervous system. The pharmacologically active agents can diffuse to varying regions of the brain and mediate their effects.

In a particular embodiment, the invention is a method of delivering an amphetamine compound or a methamphetamine compound to an individual by administering to the individual a carbamoyl ester. The carbamoyl ester inhibits a cholinesterase and comprises an amine group that, upon hydrolysis, e.g., by reaction with the cholinesterase, becomes the amphetamine compound, thereby delivering the amphetamine compound to the tissue.

In an additional embodiment, the invention is a method of treating glaucoma in an individual, comprising the step of administering to the individual a carbamoyl ester. The carbamoyl ester inhibits a cholinesterase, thereby treating the glaucoma in the individual, and includes an amine group that, upon hydrolysis, e.g., by reaction with the cholinesterase, becomes at least a component of a pharmacologically active agent that further treats the glaucoma in the individual.

In still another embodiment, the invention includes pharmaceutical compositions comprising the carbamoyl esters described herein. The pharmaceutical composition comprises a carbamoyl ester that inhibits a cholinesterase, wherein the carbamoyl ester includes an amine group that, upon hydrolysis, e.g., by reaction with the cholinesterase, becomes at least a component of a pharmacologically active agent.

In a particular embodiment, the carbamoyl ester of the pharmaceutical composition has the following structure:

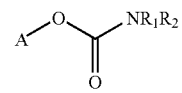

wherein A is selected from the group consisting of an unsubstituted aryl, a substituted aryl, an unsubstituted heteroaryl and a substituted heteroaryl; and $R_1$ and $R_2$ are each, independently or in combination, selected from the group consisting of hydrogen, unsubstituted alkyl, substituted alkyl, unsubstituted aralkyl, substituted aralkyl, unsubstituted heteroalkyl, substituted heteroalkyl, unsubstituted heteroaralkyl, substituted heteroaralkyl unsubstituted aryl, substituted aryl, unsubstituted heteroaryl, substituted heteroaryl, unsubstituted cycloalkyl, substituted cycloalkyl, unsubstituted heterocycloalkyl and substituted heterocycloalkyl.

In another embodiment, the carbamoyl ester of the pharmaceutical composition is not (3aS-cis)-1,2,3,3a,8,8a-hexahydro,-1,3a,8-trimethyl pyrrolo[2,3-b]-indo-5-ol, 4-pyridinyl carbamate ester, (3aS-cis)-1,2,3,3a,8,8a hexahydro-1, 3a,8-trimethyl-pyrrolo[2,3-b]indol-5-ol,(2-phenyl)ethyl carbamate ester, (3aS-cis)-1,2,3,3a,8,8a-hexahydro-1,3,8-trimethyl-pyrolo[2,3-b]indol-5-ol[1-(1-naphthyl)ethyl]carbamate ester, 7-bromo-(3aS-cis)-1,2,3,3a,8,8a-hexahydro-1, 3a,8-trimethyl pyrrolo[2,3-b]indol-5-ol, n-heptyl carbamate ester, or a tetrahydroisoquinolinyl carbamate ester.

The carbamoyl esters of the invention can be employed in the methods, pharmaceutical compositions, kits and assays of the invention in a single dose or in multiple doses. The multiple doses can be administered as multiple doses in a single day, as a single daily dose administered for more than one day, as multiple doses administered daily for more than one day, or as a single dose on any given day followed or preceded by multiple doses in the intervening days. The multiple doses can be administered for a day, days, a week, weeks, a month, months, a year or years.

The carbamoyl esters of the invention can be administered in the methods of the invention to an individual acutely (briefly or short-term) or chronically (prolonged or long-term). For example, the carbamoyl esters of the invention can be used in methods to treat an individual by administering the carbamoyl ester to the individual once a day, multiple times (e.g., 2, 3, 4) in a day, for a day, days, a week, weeks, a month, months or years.

In one embodiment, the dose of the carbamoyl ester can be about 0.1 mg, about 1 mg, about 2.5 mg, about 5 mg, about 10 mg, about 15 mg, about 20 mg, about 25 mg, about 40 mg, about 50 mg, about 75 mg, about 90 mg, about 100 mg, about 150 mg, about 200 mg, about 250 mg, about 500 mg, about 750 mg or about 1000 mg.

In another embodiment, the dose of the carbamoyl ester can be between about 1 mg to about 100 mg; between about 2 mg to about 50 mg; or between about 5 mg to about 25 mg.

In still another embodiment, each dose of a multiple dose can be about 0.1 mg, about 1 mg, about 2.5 mg, about 5 mg, about 10 mg, about 20 mg, about 25 mg, about 40 mg, about 50 mg, about 75 mg, about 90 mg, about 100 mg, about 150 mg, about 200 mg, about 250 mg, about 500 mg, about 750 mg or about 1000 mg.

In a further embodiment, each dose of a multiple dose can be between about 1 mg to about 100 mg; between about 2 mg to about 50 mg; or between about 5 mg to about 25 mg.

The carbamoyl ester and the pharmacologically active agent are administered in the methods of the invention or employed in the assays and kits of the invention in an effective amount. The term "effective amount," "amount effective," or "therapeutically effective amount," when referring to the amount of the carbamoyl ester or pharmacologically active agent, is defined as that amount, or dose, of the carbamoyl ester or pharmacologically active agent that is sufficient for therapeutic efficacy (e.g., an amount sufficient to treat a nervous system condition in an individual; increase ACh in an in vitro sample, in a tissue or in an individual; increase transmission between two or more neurons; treat a cholinergic deficiency; treat an impairment in memory; treat an impairment in cognition; deliver a pharmacologically active agent to a tissue or an individual).

The carbamoyl ester can optionally be used in the methods, kits and assays of the invention with an acceptable carrier. The selection of an acceptable carrier will depend upon the method, kit or assay. For example, an acceptable carrier in an in vitro method, assay or kit can be saline, a suitable buffer or cell culture media.

The carbamoyl esters of the invention can be administered alone or as admixtures with conventional excipients, for example, pharmaceutically, or physiologically, acceptable organic, or inorganic carrier substances suitable for enteral or parenteral application which do not deleteriously react with the compound employed in the method. Suitable pharmaceutically acceptable carriers include water, salt solutions (such as Ringer's solution), alcohols, oils, gelatins and carbohydrates such as lactose, amylose or starch, fatty acid esters, hydroxymethycellulose, and polyvinyl pyrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances which do not deleteriously react with the compounds employed in the methods of the invention. The preparations can also be combined, when desired, with other active substances to reduce metabolic degradation.

Preferred methods of administration of the carbamoyl esters are oral administration (such as a tablet or capsule). The carbamoyl ester alone, or when combined with an admixture, can be administered in a single or in more than one dose over a period of time to confer the desired effect (e.g., improve a nervous system condition, increase acetylcholine, increase transmission between two or more neurons, treat a cholinergic deficiency, treat a memory impairment, treat a cognitive impairment, deliver a pharmacologically active agent).

The carbamoyl esters can be administered to a target site in an individual. The target site selected can depend on the condition to be treated. For example, a local injection in a skeletal muscle (the target site) can be employed to treat a peripheral nervous system condition, or local injection in the cerebral spinal fluid, sinuses or ventricles of the brain (target sites) can be employed to treat a central nervous system condition. In another example an eye drop, an ointment, a gel or an ocular injection containing the carbamoyl ester can be employed to treat glaucoma in an individual.

When parenteral application is needed or desired, particularly suitable admixtures for the carbamoyl esters are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampules are convenient unit dosages. The carbamoyl esters employed in the methods, assays or kits of the invention can also be incorporated into liposomes or administered by transdermal pumps or patches. Pharmaceutical admixtures suitable for use in the present invention are well-known to those of skill in the art and are described, for example, in Pharmaceutical Sciences (17th Ed., Mack Pub. Co., Easton, Pa.) and WO 96/05309, the teachings of which are hereby incorporated by reference.

The dosage and frequency (single or multiple doses) administered to an individual can vary depending upon a variety of factors, including, for example, the nervous system condition to be treated, the type of cholinergic deficiency in the individual, the duration of the nervous system condition, the degree of memory impairment (e.g., impairment in memory consolidation, impairment in short-term memory), the degree of cognitive impairment (e.g., attention, alertness, executive function, wakefulness, arousal, vigilance, executive function, reaction time), the pharmacologically active agent to be delivered or cognition; size, age, sex, health, body weight, body mass index and diet of the individual; nature and extent of symptoms of the condition or impairment in memory or cognition, kind of concurrent treatment, complications from the condition or impairment, or other health-related problems of the human being treated.

Other therapeutic regimens or agents can be used in conjunction with the methods and carbamoyl esters employed in the methods of the invention. Adjustment and manipulation of established dosages (e.g., frequency and duration) are well within the ability of those skilled in the art.

The present invention is further illustrated by the following examples, which are not intended to be limiting in any way.

EXEMPLIFICATION

Example 1

Scheme I. Synthesis of a Carbamoyl Ester

Seventy three milligrams (73 mg) of NaH (60% dispersion in mineral oil) was added to a solution of 0.3 g (1.82 mmol) (−)-3'-hydroxyphenylethyldimethylamine (1) in 15 ml toluene. The solution was stirred at room temperature for 30 min and then 0.33 g of carbonyldiimidazole (CDI) (2.0 mmol) was added in one portion, and heated to 80° C. for 2 hours. dl-Amphetamine (2) sulfate (0.335 g, 1.82 mmol) was then added and the mixture was stirred at room temperature for 2 days. Distilled water (20 ml) and 15 ml of a 1M HCl solution were added to the reaction mixture and the aqueous and organic layers separated. The aqueous layer was washed with chloroform, basified with 1 M NaOH to pH ~11 and extracted with ether. The ether layer was dried over sodium sulfate, evaporated and purified with a silica gel column (eluted with 3% methanol and 1% triethylamine in ethyl acetate) to yield 0.27 g of the carbamoyl ester (3) (0.83 mmol, 46% yield).

The carbamoyl ester (3) was confirmed by NMR. $^1$H-NMR (CDCl$_3$, 300 MHz): δ 1.146 (d, 3H, J=6.6 Hz, CH$_3$), 1.312 (d, 3H, J=6.7 Hz, CH$_3$), 2.153 (s, 6H, 2×CH$_3$), 2.721 (dd, 1H, J=13.4 and 7.2 Hz, CHH), 2.866 (dd, 1H, J=13.4 and 5.9 Hz, CHH), 3.218 (q, 1H, J=6.6 Hz, CH), 3.960-4.936 (m, 1H, CH), 4.870 (bd, 1H, J=7.7 Hz, NH), 6.943 (bd, 1H, J=7.2 Hz, CH arom.), 6.993 (bs, 1H, CH arom.), 7.078 (bd, 1H, J=7.7 Hz, CH arom.) 7.156-7.291 (m, 6H, CH arom.).

33

Scheme I

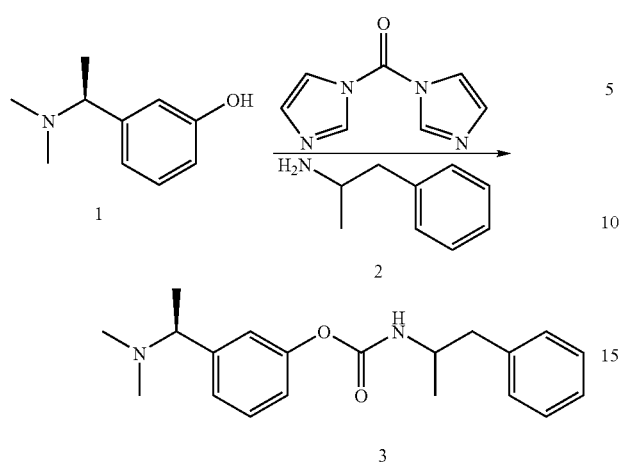

Example 2

Scheme II. Synthesis of a Carbamoyl Ester (S)-(−)-3'-hydroxyphenylethyldimethylamine (96 mg, 0.58 mmol) (1) was dissolved in 4 ml of dry ethyl acetate. N,N'-carbonyldiimidazole powder (283 mg, 1.74 mmol) was added and the mixture stirred at room temperature for 20 h. Acetic acid (313 mg, 5.22 mmol) was then added to the mixture, followed by the addition of 162 mg (−)-atomoxetine (4, 0.63 mmol). The resulting mixture was stirred at room temperature overnight. Saturated sodium bicarbonate solution was added to the mixture and the aqueous and organic layers separated. The aqueous layer was extracted twice with ethyl acetate. The organic layers were combined, dried over NaHCO3, evaporated and purified with a silica gel column (eluted with 25% ethyl acetate in hexane with 1% triethylamine) to yield 101 mg of the carbamoyl ester (5) (0.23 mmol, 39.0% yield). Free base 5 was converted into the hydrochloride salt following the procedure described in Example 14.

The carbamoyl ester (5) was confirmed by NMR. $^1$H-NMR of the HCl salt (CDCl$_3$, 400 MHz): δ 1.808 and 1.825 (d, 3H, J=6.8 Hz, CH$_3$), 2.090-2.320 (m, 2H), 2.262 (ma) and 2.325 (mi) (s, 3H, CH$_3$), 2.506-2.541 (m, 3H, CH3), 2.658-2.698 (m, 3H, CH3), 3.002 (ma) and 3.082 (mi) (s, 3H, CH3), 3.520-3.575 (m, 1H, CH), 3.662-3.700 and 3.892-3.961 (m, 1H, CH), 4.048-4.123 (m, 1H, CH), 5.180-5.252 (m, 1H, CH), 6.535-6.582 (m, 1H, CH arom.), 6.729-6.787 and 6.902-6.957 (m, 3H, 3×CH arom.), 7.007-7.086 (m, 2H, 2×CH arom.), 7.224-7.428 (m, 7H, 7×CH arom.), 12.620 (bs, 1H, Hcl).

Scheme II

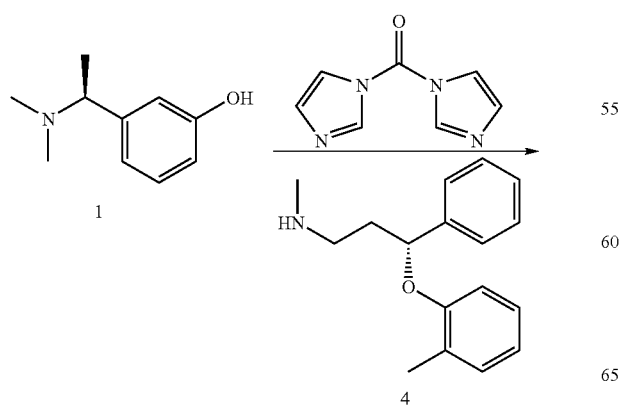

34

-continued

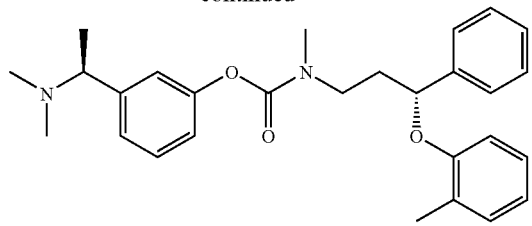

Example 3

Scheme III. Synthesis of a Carbamoyl Ester 4-nitrophenychloroformate powder (0.179 g, 0.86 mmol) was added to a solution of 0.12 g (0.72 mmol) (−)-3'-hydroxyphenylethyldimethylamine (1) and 0.22 g (2.17 mmol) triethylamine in 10 ml of dry dichloromethane (0.86 mmol) at 0° C. The solution was stirred at 0° C. for 5 min followed by stirring at room temperature for an additional 30 minutes. A solution of 0.107 g 1-methamphetamine (6) in 2 ml of dry dichloromethane was then added, and the resulting solution stirred at room temperature for 2 hours. The solvent was evaporated and the residue applied to a silica gel column. The carbamoyl ester (7) was eluted with 3% acetone in ethyl acetate containing 1% triethylamine. Fractions containing the carbamoyl ester (7) were combined and concentrated to yield 0.15 g of the carbamoyl ester (7) (0.44 mmol, 61% yield).

The carbamoyl ester (7) was confirmed by NMR. $^1$H-NMR (CDCl3, 300 MHz): δ 1.192 (mi) and 1.275 (ma) (d, 3H, J=6.8 Hz, CH$_3$), 1.305 and 1.326 (d, 3H, J=3.0 Hz, CH$_3$), 2.162 and 2.167 (s, 6H, 2×CH$_3$), 2.746 (dd, 1H, J=13.7 and 6.8 Hz, CHH), 2.850 (dd, 1H, J=13.7 and 6.8 Hz, CHH), 2.868 and 2.886 (s, 3H, CH$_3$), 3.165-3.217 (m, 1H, CH), 4.558-4.633 (m, 1H, CH), 6.665 and 6.855 (bd, 1H, J=7.9 Hz, CH arom.), 6.723 and 6.928 (bs, 1H, CH arom.), 7.065 (bd, 1H, J=7.2 Hz, CH arom.), 7.176-7.305 (m, 6H, CH arom.).

Scheme III

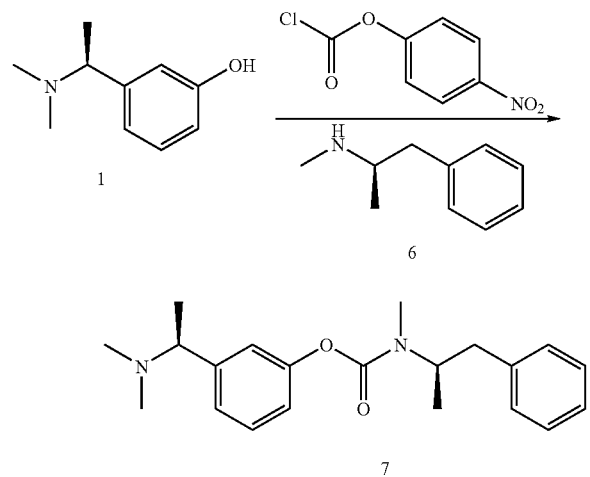

Example 4

Scheme IV. Synthesis of a Carbamoyl Ester

At room temperature, diisopropylethylamine (5.16 g, 40 mmol) and CDI powder (6.48 g, 40 mmol) were added to a suspension of 7.34 g of 1-amphetamine sulfate (8) (40 mmol) in 140 ml of dichloromethane. The resulting mixture was stirred at room temperature for 1 h. (−)-α-3'-hydroxyphenylethyldimethylamine (1) (3.3 g, 20 mmol), which had been mixed with 0.8 g sodium hydride (60% dispersion in mineral oil) in dry toluene (120 ml) for 30 minutes, was added to the mixture and the dichloromethane removed under reduced pressure. The resulting suspension was heated to 85° C. overnight with stirring. The reaction mixture was extracted with 0.5 M HCl (200 ml). The aqueous layer was washed with ethyl acetate, basified at 0° C. to pH ~11 with sodium bicarbonate and 0.5 N NaOH and extracted with ethyl acetate (3×100 ml). The organic layers were combined, dried over sodium sulfate and evaporated. The residue was purified with a silica gel column. Elution with a mixture of 20-30% ethyl acetate with 1% triethylamine in hexane yielded 1.53 g of the carbamoyl ester (9) (4.7 mmol, 23.5% yield).

The carbamoyl ester (9) was confirmed by NMR. $^1$H-NMR (CDCl3, 300 MHz): δ 1.179 (d, 3H, J=6.6 Hz, CH$_3$), 1.331 (d, 3H, J=6.7 Hz, CH$_3$), 2.174 (s, 6H, 2×CH$_3$), 2.789 (dd, 1H, J=13.4 and 7.2 Hz, CHH), 2.832 (dd, 1H, J=13.4 and 5.9 Hz, CHH), 3.228 (q, 1H, J=6.7 Hz, CH), 3.980-4.062 (m, 1H, CH), 4.856 (bd, 1H, J=7.2 Hz, NH), 6.955 (bd, 1H, J=7.4 Hz, CH arom.), 7.018 (bs, 1H, CH arom.), 7.095 (bd, 1H, J=7.7 Hz, CH arom.) 7.186-7.303 (m, 6H, CH arom.).

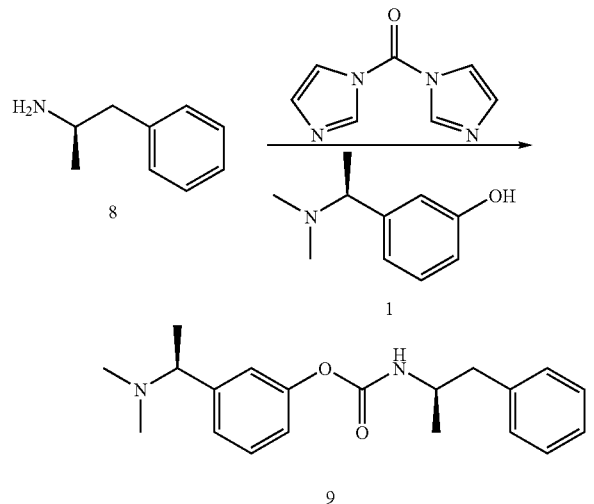

Scheme IV

Example 5

Scheme V. Synthesis of a Carbamoyl Ester (S)-(−)-3'-hydroxyphenylethyldimethylamine (1) (1.2 g, 7.3 mmol) was dissolved in 20 ml of dry ethyl acetate. N,N'-carbonyldiimidazole powder (2.37 g, 14.6 mmol) was added and the mixture stirred at 85° C. overnight. After cooling to 0° C., 3.3 g of acetic acid (55.0 mmol) was added, followed by the addition of 2.8 g of 1-amphetamine (8) (20.7 mmol). The mixture was stirred at room temperature for 36 h. Water (20 ml) and 1M HCl (20 ml) were added and the aqueous and organic layers separated. The organic layer was extracted with 0.5M HCl. The aqueous layers were combined and washed with ether twice, basified with NaHCO$_3$ and 0.5 N NaOH to pH ~11 and extracted with ether. The ether layer was dried over NaHCO$_3$, evaporated and purified with silica gel chromatography. Elution with a mixture of 25% ethyl acetate with 1% triethylamine in hexane yielded 0.93 g of the carbamoyl ester (9) (2.85 mmol, 39% yield).

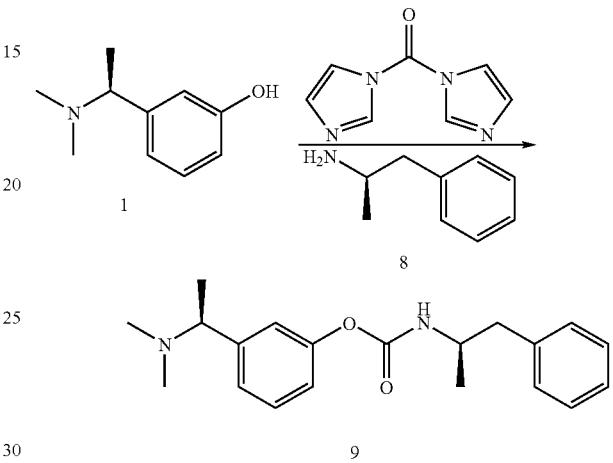

Scheme V

Example 6

Scheme VI. Synthesis of a Carbamoyl Ester

Triphosgene (85.5 mg, 0.28 mmol) was dissolved in 2 ml of dry dichloromethane. To this solution, a mixture of 145 mg of desmethylselegeline (10) (0.84 mmol) and 110 mg of diisopropylethylamine (DIEA) (0.85 mol) in 1 ml of dry dichloromethane was added at 0° C. and allowed to react for 10 minutes. The mixture was stirred at room temperature for 60 hours, and subsequently added to a suspension of (−)-α-3'-hydroxyphenylethyldimethylamine (1) (92 mg, 0.55 mmol) and sodium hydride (68 mg, 60% dispersion in mineral oil) in dry acetonitrile, which had been stirred at room temperature for 1 hour. The resulting mixture was stirred at room temperature overnight. The solvents of the above mixture were removed under reduced pressure. The residue was dissolved in 0.5 M HCl and washed with ether. The aqueous layer was basified with sodium bicarbonate and extracted with ethyl acetate (3×20 ml). The organic layer was washed with 0.5 N NaOH (200 ml), dried over sodium sulfate and evaporated. The residue was purified with a silica gel column (eluted with 30-60% ethyl acetate in hexane with 1% triethylamine) to yield 185 mg of the carbamoyl ester (11) (0.508 mmol, 92.3% yield).

The carbamoyl ester (11) was confirmed by NMR. $^1$H-NMR (CDCl3, 300 MHz): δ 1.339 (d, 3H, J=6.6 Hz, CH$_3$), 1.327-1.415 (m, 3H, CH$_3$), 2.187 (s, 6H, 2×CH$_3$), 2.215-2.258 (m, 1H, CH), 2.843-2.870 (m, 1H, CH), 3.063 (dd, 1H, J=13.5 and 7.5 Hz, CHH), 3.230 (q, 1H, J=6.6 Hz, CH), 4.043-4.118 (m, 2H, 2×CH), 4.372-4.411 (m, 1H, CH), 6.846-7.024 (m, 2H, 2×CH arom.), 7.108 (bd, 1H, J=7.7 Hz, CH arom.), 7.202-7.313 (m, 6H, CH arom.).

Scheme VI

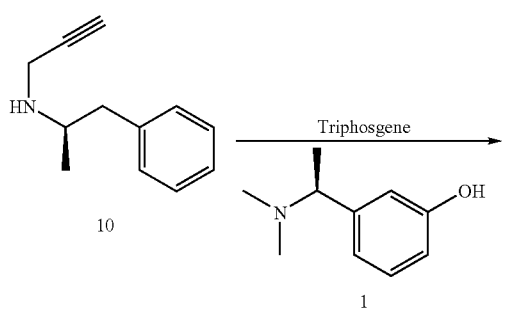

Example 7

Scheme VII. Synthesis of a Carbamoyl Ester

Triphosgene (140 mg, 0.47 mmol) was dissolved in 6 ml of dry dichloromethane. To this solution, a mixture of 204.5 mg of l-methamphetamine (6, 1.37 mmol) and 177 mg of diisopropylethylamine (DIEA) (1.37 mol) in 2 ml of dry dichloromethane was added at 0° C. and reacted for 10 minutes. The mixture was stirred at room temperature for 2 days, and subsequently added to a solution of eseroline (12) (153 mg, 0.70 mmol) and 4-dimethylaminopyridine (268 mg) in 5 ml of dry acetonitrile. The resulting mixture was stirred at room temperature overnight. The solvents of the above mixture were removed under reduced pressure. The residue was dissolved in sodium bicarbonate solution and extracted with ethyl acetate (3×20 ml). The organic layer was dried over sodium sulfate and evaporated. The residue was purified with a silica gel column (eluted with 30-60% ethyl acetate in hexane with 1% triethylamine) to yield 40 mg of the carbamoyl ester (13) (0.10 mmol, 14% yield).

The carbamoyl ester (13) was confirmed by NMR. $^1$H-NMR (CDCl3, 300 MHz): δ 1.177 (mi) and 1.261 (ma) (d, 3H, J=6.7 Hz, CH$_3$), 1.386 (ma) and 1.397 (mi) (s, 3H, CH$_3$), 1.866-1.932 (m, 2H), 2.505 (s, 3H, CH3), 2.542-2.767 (m, 3H), 2.803-2.870 (m, 1H), 2.860 (s, 6H, 2×CH$_3$), 4.078 (s, 1H), 4.050-4.610 (m, 1H, CH), 6.254 (ma) and 6.285 (mi) (d, 1H, J=8.4 Hz, CH arom.), 6.359 (ma) and 6.591 (mi) (d, 1H, J=2.2 Hz, CH arom.), 6.460 (ma) and 6.666 (mi) (dd, 1H, J=8.4 and 2.2 Hz, CH arom.), 7.170-7.300 (m, 5H, CH arom.).

Scheme VII

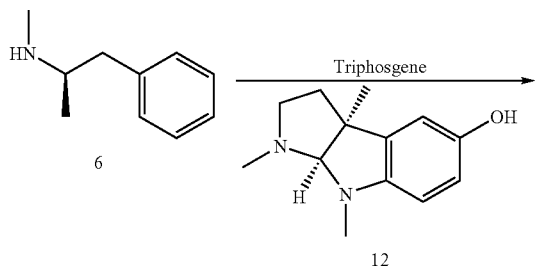

Example 8

Scheme VIII. Synthesis of a Carbamoyl Ester

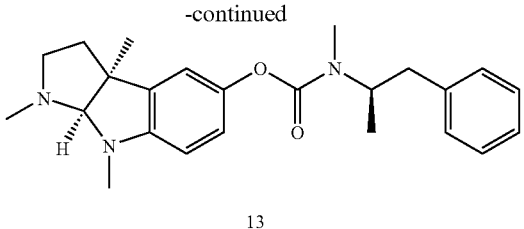

Eseroline (12) (57 mg, 0.26 mmol) was dissolved in 4 ml dry ethyl acetate. CDI (106 mg, 0.65 mmol) was added and the mixture stirred at room temperature for 2 hours. Acetic acid (117 mg, 1.95 mmol) was added followed by 85 mg (0.57 mmol) of l-methamphetamine (6). The resulting mixture was stirred at room temperature for 24 h under argon. The reddish reaction mixture was washed with water. The aqueous solution was extracted with ethyl acetate, neutralized with 0.5 N NaOH to pH ~8 and extracted with ethyl acetate (3×50 ml). All the organic layers were combined, dried over sodium sulfate, concentrated and purified with a silica gel column (eluted with 30% ethyl acetate and 1% triethylamine in hexane) to yield 38.4 mg of the carbamoyl ester (13) (0.1 mmol, 38.5% yield). The product was identical to carbamoyl ester (13) obtained in Example 7.

Scheme VIII

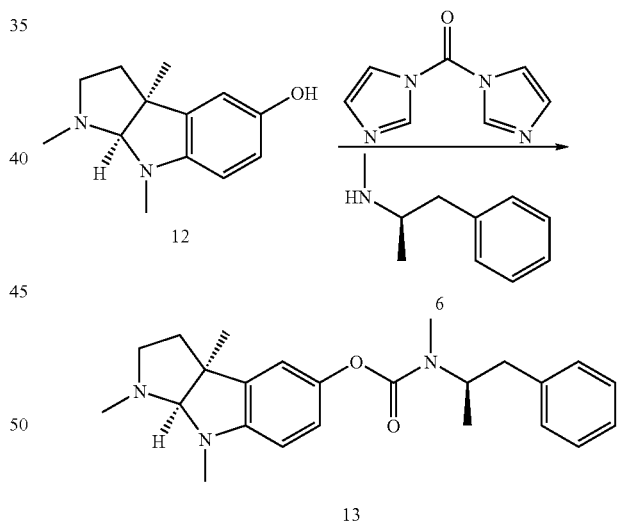

Example 9

Scheme IX. Synthesis of a Carbamoyl Ester

Eseroline (12) (1.14 g, 5.2 mmol) was dissolved in 30 ml of dry ethyl acetate. CDI (1.7 g, 10.5 mmol) was added and the mixture stirred at room temperature for 2 hours. Acetic acid (1.26 g, 21 mmol) was added followed by 1.46 g (7.5 mmol) of l-amphetamine (8) acetate salt. The mixture was stirred at room temperature for 24 h under argon. The reaction mixture was basified with 0.5 N NaOH to pH ~8, and extracted with ethyl acetate (3×100 ml). All the organic layers were combined, dried over sodium sulfate, concentrated and purified with a silica gel column (eluted with 30% ethyl acetate and 1% triethylamine in hexane) to yield 1.0 g of carbamoyl ester (14) (2.64 mmol, 50.6% yield).

The resulting carbamoyl ester (14) was confirmed by NMR. $^1$H-NMR (CDCl3, 300 MHz): δ 1.156 (d, 3H, J=6.5 Hz, CH$_3$), 1.400 (s, 3H, CH3), 1.892-1.939 (m, 2H), 2.513 (s, 3H, CH$_3$), 2.568-2.767 (m, 3H), 2.853-2.890 (m, 1H), 2.885 (s, 3H, CH$_3$), 3.990-4.064 (m, 1H, CH), 4.085 (s, 1H), 4.847 (bd, 1H, J=7.4 Hz, NH), 6.298 (d, 1H, J=8.3 Hz, CH arom.), 6.699 (bs, 1H, CH arom.), 6.740 (bd, 1H, J=8.3 Hz, CH arom.), 7.178-7.317 (m, 5H, CH arom.).

Scheme IX

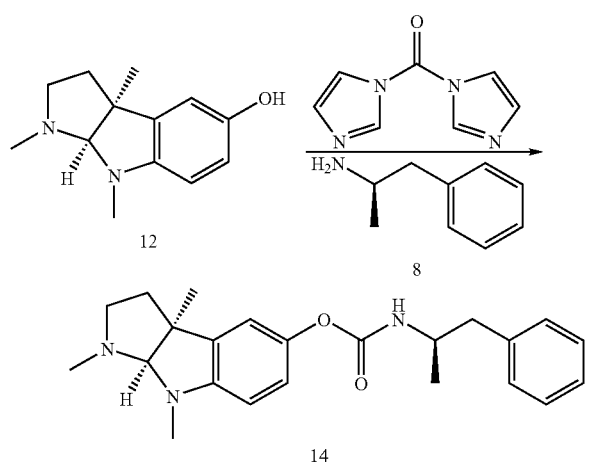

Example 10

Scheme X. Synthesis of a Carbamoyl Ester (R)-(+)-3'-hydroxyphenylethyldimethylamine (15) (95 mg, 0.57 mmol) was dissolved in 4 ml of dry ethyl acetate. N,N'-carbonyldiimidazole powder (250 mg, 1.54 mmol) was added and the mixture was stirred at 85° C. overnight. After cooling down to 0° C., 250 mg of acetic acid (4.17 mmol) was added, followed by the addition of 158 mg of 1-methamphetamine (6) (1.06 mmol). The mixture was stirred at room temperature for 36 h. Water (20 ml) and 1M HCl (20 ml) were added and the layers were separated. The organic layer was extracted with 0.5M HCl. The aqueous layers were combined, washed twice with ether and basified with NaHCO3 and 0.5 N NaOH to pH ~11, followed by extraction with ether. The ether layer was dried over NaHCO3, evaporated and purified with a silica gel chromatography (eluted with 25% ethyl acetate in hexane with 1% triethylamine) to yield 80 mg of carbamoyl ester (16) (0.23 mmol, 41.2% yield).

The carbamoyl ester (16) was confirmed by NMR. $^1$H-NMR (CDCl3, 400 MHz): δ 1.197 and 1.276 (d, 3H, J=6.8 Hz, CH$_3$), 1.314 and 1.328 (d, 3H, J=3.0 Hz, CH$_3$), 2.162 and 2.167 (s, 6H, 2×CH$_3$), 2.752 (dd, 1H, J=13.6 and 6.4 Hz, CHH), 2.845 (dd, 1H, J=13.6 and 8.8 Hz, CHH), 2.869 and 2.887 (s, 3H, CH$_3$), 3.170-3.240 (m, 1H, CH), 4.562-4.626 (m, 1H, CH), 6.671 and 6.854 (bd, 1H, J=7.8 Hz, CH arom.), 6.751 and 6.932 (bs, 1H, CH arom.), 7.068 (bd, 1H, J=7.2 Hz, CH arom.), 7.184-7.301 (m, 6H, CH arom.).

Scheme X

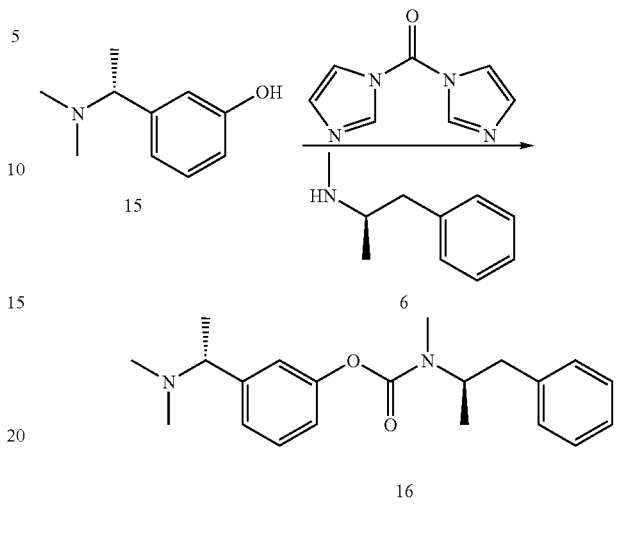

Example 11

Scheme XI. Synthesis of a Carbamoyl Ester (S)-(−)-3'-hydroxyphenylethyldimethylamine (1) (145 mg, 0.88 mmol) was dissolved in 4 ml of dry ethyl acetate. N,N'-carbonyldiimidazole powder (356 mg, 2.20 mmol) was added and the mixture stirred at room temperature for 20 h. Acetic acid (395 mg, 6.58 mmol) was added, followed by the addition of 283 mg of 2-phenylethylamine (17, 2.34 mmol). The mixture was stirred at room temperature overnight. Water (10 ml) and 1M HCl (10 ml) added and the layers separated. The organic layer was extracted with 0.5M HCl. The aqueous layers were combined, washed with ether twice and basified with NaHCO$_3$ and 0.5 N NaOH to pH ~11, followed by extraction with ether. The ether layer was dried over NaHCO$_3$, evaporated and purified with a silica gel column. Elution with 25% ethyl acetate in hexane with 1% triethylamine to yield 90 mg of carbamoyl ester (18) (0.29 mmol, 32.7% yield).

The carbamoyl ester (18) was confirmed by NMR. $^1$H-NMR (CDCl3, 300 MHz): δ 1.328 (d, 3H, J=6.7 Hz, CH$_3$), 2.169 (s, 6H, 2×CH$_3$), 2.860 (t, 2H, J=6.8 Hz, CH$_2$), 3.231 (q, 1H, J=6.7 Hz, CH), 3.466-3.532 (m, 2H, CH$_2$), 5.002 (bs, 1H, NH), 6.966 (dd, 1H, J=8.0 and 1.4 Hz, CH arom.), 7.030 (bs, 1H, CH arom.), 7.092 (bd, 1H, J=7.7 Hz, CH arom.) 7.183-7.334 (m, 6H, CH arom.).

Scheme XI

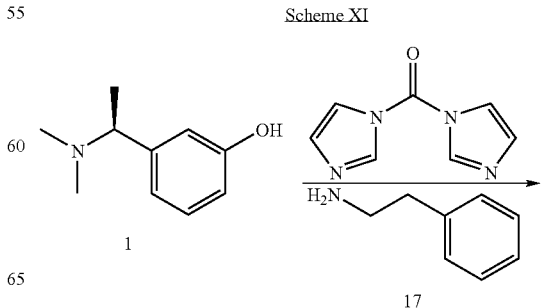

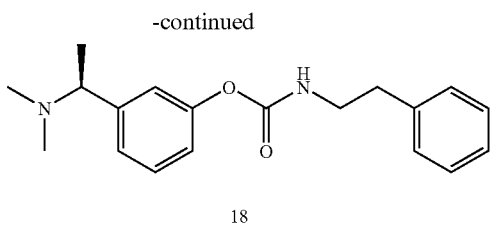

18

Example 12

Scheme XII. Synthesis of a Carbamoyl Ester (S)-(−)-3'-hydroxyphenylethyldimethylamine (1) (81 mg, 0.49 mmol) was dissolved in 4 ml of dry ethyl acetate. N,N'-carbonyldiimidazole powder (199 mg, 1.23 mmol) was added and the mixture was stirred at room temperature for 20 h. Acetic acid (184 mg, 3.07 mmol) was added, followed by the addition of 186 mg of d-amphetamine (19) acetate salt (0.96 mmol). The mixture was stirred at room temperature overnight. Water (5 ml) and 1M HCl (5 ml) were added and the aqueous and organic layers separated. The organic layer was extracted with 0.5M HCl. The aqueous layers were combined, washed with ether twice and basified with NaHCO₃ and 0.5 N NaOH to pH ~11, followed by extraction with ether. The ether layer was dried over NaHCO₃, evaporated and purified with a silica gel column (eluted with 25% ethyl acetate in hexane with 1% triethylamine) to yield 95 mg of carbamoyl ester (20) (0.29 mmol, 59.4% yield).

The carbamoyl ester (20) was confirmed by NMR. $^1$H-NMR (CDCl3, 300 MHz): δ 1.192 (d, 3H, J=6.6 Hz, CH₃), 1.367 (d, 3H, J=6.7 Hz, CH₃), 2.205 (s, 6H, 2×CH₃), 2.759 (dd, 1H, J=13.4 and 7.2 Hz, CHH), 2.896 (dd, 1H, J=13.4 and 5.9 Hz, CHH), 3.295 (q, 1H, J=6.6 Hz, CH), 3.990-4.044 (m, 1H, CH), 4.847 (bd, 1H, J=7.2 Hz, NH), 6.966 (bd, 1H, J=7.4 Hz, CH arom.), 6.976 (bs, 1H, CH arom.), 7.114 (bd, 1H, J=7.7 Hz, CH arom.) 7.191-7.324 (m, 6H, CH arom.).

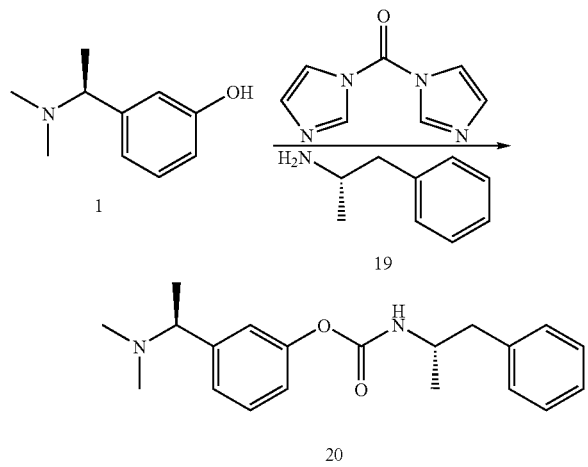

Scheme XII

Example 13

Scheme XIII. Synthesis of a Carbamoyl Ester (R)-(+)-3'-hydroxyphenylethyldimethylamine (15) (195 mg, 1.18 mmol) was dissolved in 7 ml of dry ethyl acetate. N,N'-carbonyldiimidazole powder (250 mg, 1.54 mmol) was added and the mixture was stirred at 85° C. overnight. After cooling to 0° C., 177 mg of acetic acid (2.95 mmol) was added, followed by the addition of 276 mg of l-amphetamine (8) sulfate (1.50 mmol). The mixture was stirred at room temperature for 36 h. Water (10 ml) and 1M HCl (10 ml) were added and the aqueous and organic layers separated. The organic layer was extracted with 0.5M HCl. The aqueous layers were combined, washed with ether twice and basified with NaHCO₃ and 0.5 N NaOH to pH ~11, followed by extraction with ether. The ether layer was dried over NaHCO₃, evaporated and purified with a silica gel column (eluted with 25% ethyl acetate in hexane with 1% triethylamine) to yield 100 mg of carbamoyl ester (21) (0.31 mmol, 26.0% yield).

The carbamoyl ester (21) was confirmed by NMR. $^1$H-NMR (CDCl3, 400 MHz): δ 1.179 (d, 3H, J=6.6 Hz, CH₃), 1.342 (d, 3H, J=6.7 Hz, CH₃), 2.183 (s, 6H, 2×CH₃), 2.755 (dd, 1H, J=13.5 and 7.2 Hz, CHH), 2.896 (dd, 1H, J=13.5 and 5.6 Hz, CHH), 3.249 (q, 1H, J=6.7 Hz, CH), 3.960-4.936 (m, 1H, CH), 4.890 (bd, 1H, J=7.9 Hz, NH), 6.974 (bd, 1H, J=7.9 Hz, CH arom.), 7.021 (bs, 1H, CH arom.), 7.102 (bd, 1H, J=7.7 Hz, CH arom.) 7.190-7.322 (m, 6H, CH arom.).

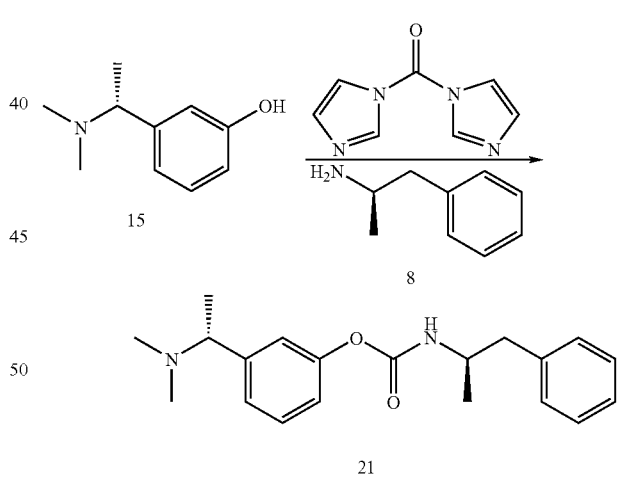

Scheme XIII

Example 14

Preparation of Hydrochloride Salts of Carbamoyl Esters

The carbamoyl ester was dissolved in chloroform (3 ml per mmol). A solution of 1M HCl in ether (1.5-2 molar equivalents) was added dropwise at 0° C. Upon completion of addition of hydrochloric acid, the mixture was allowed to warm to room temperature. Solvents were removed by evaporation and the residue dried under vacuum to yield the hydrochloride salt of the carbamoyl ester visible as a white to off-white solid.

Example 15

Carbamoyl Esters Inhibit Acetylcholinesterase in Vitro

All reagents employed in these experiment were of analytical grade. Acetylthiocholine iodide and 5,5'-dithiobis-(2-nitro)benzoic acid (DTNB) and human recombinant acetylcholinesterase (C1682) were purchased from Sigma Chemical Co (St. Louis, Mo.).

Acetylcholinesterase activity of carbamoyl esters was determined at 25° C. by a modification of the colorimetric method of Ellmann, et al. (*Biochem. Pharmacol.,* 7:88-95 (1961)). The enzyme, carbamoyl ester or stigmine and buffer were preincubated for 30 minutes. At the end of the preincubation period, the substrate acetylthiocholine was added. The final assay mixture contained 10 mM Tris-buffer (pH 8), 0.3 mM Acetylthiocholine and 0.33 mM DTNB and 0.08 U/ml enzyme. At least five (5) different concentrations of the carbamoyl ester or stigmine were assayed per IC50 experiment.

Hydrolysis of acetylthiocholine was monitored indirectly by measurement of the formation of the conjugate between thiocholine and DTNB. Optical density at 405 nm was recorded during 5 minutes employing a microplate spectrophotometer (Polarstar, BMG Labtech) and plotted against time. The inverse of the initial rates for a range of inhibitor concentrations was plotted against concentration (Dixon Plot) to give the IC50 value (the concentration at which enzyme activity is inhibited by 50%) as the opposite value of the x-intercept (Burlingham, et al., *J. Chem. Ed.,* 80:214-218 (2003)).

The results are summarized as follows:

| Compound | IC50 |
|---|---|
| Rivastigmine | 2,615 nM |
| 5 | 460 nM |
| 7 | 302 nM |
| 9 | 404 nM |
| 13 | 5,440 nM |
| 14 | 253 nM |
| 20 | 449 nM |

These data show that the carbamoyl esters of the invention inhibit acetylcholinesterase in vitro. Inhibition of acetylcholinesterase by carbamoyl esters can be greater than inhibition of acetycholinesterase by a stigmine, such as rivastigmine. Carbamoyl esters synthesized from stigmines resulted in similar or increased activity compared to the stigmine. For example, the carbamoyl ester (14) resulted in a 10 fold increase in enzymatic activity compared to rivastigmine. Thus, structural alterations in stigmines, carbamoyl esters with known enzymatic activity, did not decrease or inhibit the enzymatic activity of the stigmine.

Example 16

Carbamoyl Esters Inhibit Cholinesterase in Brain

Male Wistar rats were injected intraperitoneally (i.p.) with rivastigmine or with carbamoyl esters 7 and 9. The dose of rivastigmine or carbamoyl ester resulted in a cholinergic behavioral effect with minimal side effects and was well-tolerated by the animals. Animals were decapitated 3 hours after injection and the brains rapidly removed. The brain tissue was diced into small pieces, placed on ice and immediately homogenized with a Polytron PT1200 (Kinematic AG) in 10 ml ice cold Tris with 0.1% Triton-X and protease inhibitors. The protease inhibitors in the extraction buffer were Antipain (10 μM), Aprotinin (5 TIU/mg protein), Bestatin (60 nm), Leupeptin (10 μM) and Pepstatin (1 μM). The final dilution of the homogenate in the final assay mixture was 120-fold.

Total cholinesterase activity was determined by a modification of the colorimetric method of Ellmann, et al. (*Biochem. Pharmacol.,* 7:88-95 (1961)), as described above. Hydrolysis of acetylthiocholine was monitored indirectly by measurement of the formation of the conjugate between thiocholine and DTNB. Optical density at 405 nm was recorded during five (5) minutes employing a a microplate spectrophotometer (Polarstar, BMG Labtech), and plotted against time. The initial rates were calculated from the slope of the linear portion of the graph.

Cholinesterase activity was normalized for protein content of the homogenate. Relative cholinesterase activity was calculated as the ratio of normalized cholinesterase activity in a rat treated with a control compound or a carbamoyl ester over normalized cholinesterase activity in saline treated rats.

These data are summarized below:

| Compound | dose | Relative ChE Activity | ChE inhibition |
|---|---|---|---|
| Rivastigmine | 2 mg/kg | 85% | 15% |
| 7 | 2 mg/kg | 62% | 38% |
| 9 | 8 mg/kg | 59% | 41% |

These data show that systemic administration of compounds of the invention results in inhibition of total cholinesterase activity in the brain of mammals. The carbamoyl esters resulted in significantly increased inhibition of cholinesterase activity in the brain compared to rivastigmine with minimal side effects. Thus, the carbamoyl esters of the invention can be employed in methods that inhibit cholinesterases with few side effects compared to currently available cholinesterase inhibitors.

Example 17

Carbamoyl Ester Alleviates Scopolamine Induced Amnesia in Multiple Trial Passive Avoidance Assay Inhibitory avoidance is used as a cognitive performance screen because the discrete nature of the task allows for precise pharmacological manipulation and for the ability to selectively study acquisition, consolidation, or recall or learned information. This task has been widely used to assess the facilitory effects of centrally acting drugs in both normal, untreated animals, and in animals made amnestic by the use of scopolamine, a muscarinic cholinergic receptor antagonist that produces marked amnesia.

The inhibitory avoidance apparatus used in these experiments consisted of a light chamber and a dark chamber, which were joined by means of a sliding guillotine door. Training involved placing a rat inside the light chamber with its head facing away from the door. Ten seconds later, the sliding door was opened, and the latency to enter the dark chamber was recorded (100 second maximum). When the rat entered the dark chamber, it received a continuous footshock (0.4 mA) through the metal grid floor until it returned to the light chamber. This sequence of events continued until the rat remained in the light chamber for a period of 100 consecutive seconds or until a maximum of 5 footshocks had been received.

Retention testing, or the ability of the rat to remember the previous events in the inhibitory avoidance apparatus, was conducted 24 hours after the initial testing. The rat was placed into the light chamber with its head facing away from the door. Ten seconds later, the door was opened, allowing the rat access to the dark chamber. No footshock was administered during retention testing. Latency to enter the dark chamber was recorded (900 seconds maximum) and used as a measure of memory.

To assess the effects of the carbamoyl esters on scopolamine-induced amnesia, rats were injected with saline or scopolamine hydrochloride (0.75 mg/kg) 30 minutes prior to training on the Inhibitory Avoidance task. Immediately following the training trial, rats were injected with saline or the carbamoyl ester.

Retention for the task in scopolamine or saline treated rats, was assessed as described above, 24 hours later. No compound (drug) was administered to the rat prior to the retention test and no shock was given during retention testing. For retention testing, the rat was placed into the light chamber. Fifteen seconds later, the door was automatically opened and latency to enter the dark compartment was measured. The latency to enter the dark chamber is the primary measure of memory on this task. Carbamoyl esters were evaluated in this protocol. Carbamoyl esters and rivastigmine were injected i.p. into rats. The table below summarizes the most effective dose (the dose that increases the latency the most) for each compound, the performance relative to the unimpaired (saline) control group as well as the performance relative to the impaired (scopolamine) group at the most effective dose.

| Compound | Dose | Performance relative to scopolamine | Performance relative to saline |
| --- | --- | --- | --- |
| Rivastigmine | 0.25 mg/kg | 301% | 123% |
| 3 | 1.4 mg/kg | 294% | 100% |
| 7 | 0.25 mg/kg | 298% | 64% |
| 9 | 0.1 mg/kg | 306% | 83% |
| 14 | 0.02 mg/kg | 186% | 51% |

These results show that systemic administration of the carbamoyl esters of the invention increases performance in an animal model of amnesia.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A carbamoyl ester that inhibits a cholinesterase, comprising an amine group that, upon hydrolysis, becomes at least a component of a pharmacologically active agent, wherein the pharmacologically active agent is an amphetamine compound, further wherein the carbamoyl ester is:

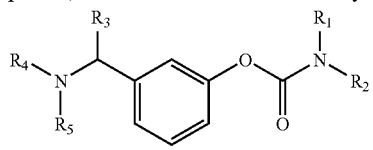

wherein
$R_1$ is selected from the group consisting of hydrogen, unsubstituted alkyl, substituted alkyl, unsubstituted aralkyl, substituted aralkyl, unsubstituted heteroalkyl, substituted heteroalkyl, unsubstituted heteroaralkyl, substituted heteroaralkyl, unsubstituted aryl, substituted aryl, unsubstituted heteroaryl, substituted heteroaryl, unsubstituted cycloalkyl, substituted cycloalkyl, unsubstituted heterocycloalkyl and substituted heterocycloalkyl;

$R_2$ is selected from the group consisting of unsubstituted aralkyl and substituted aralkyl, wherein said aralkyl group is an aryl substituent linked by a branched alkyl group having from 3-5 carbon atoms; and $R_3$, $R_4$ and $R_5$ are each, independently or in combination, selected from the group consisting of hydrogen, unsubstituted alkyl, substituted alkyl, unsubstituted aralkyl, substituted aralkyl, unsubstituted heteroalkyl, substituted heteroalkyl, unsubstituted heteroaralkyl, substituted heteroaralkyl, unsubstituted aryl, substituted aryl, unsubstituted heteroaryl, substituted heteroaryl, unsubstituted cycloalkyl, substituted cycloalkyl, unsubstituted heterocycloalkyl and substituted heterocycloalkyl.

2. The carbamoyl ester of claim 1, wherein hydrolysis occurs by reaction with an enzyme.

3. The carbamoyl ester of claim 2, wherein the enzyme is a cholinesterase.

4. The carbamoyl ester of claim 3, wherein the cholinesterase is a acetylcholinesterase.

5. The carbamoyl ester of claim 3, wherein the cholinesterase is a butylrylcholinesterase.

6. The carbamoyl ester of claim 1, wherein hydrolysis occurs by reaction with an acid.

7. The carbamoyl ester of claim 1, wherein the carbamoyl ester is:

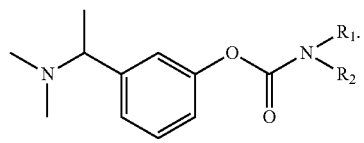

8. The carbamoyl ester of claim 7, wherein the carbamoyl ester is:

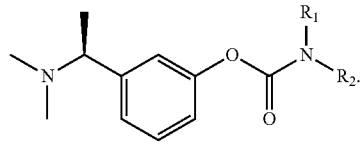

9. The carbamoyl ester of claim 1, wherein the amphetamine compound is an amphetamine.

10. The carbamoyl ester of claim 1, wherein the amphetamine compound is a methamphetamine.

11. A pharmaceutical composition comprising a carbamoyl ester that inhibits a cholinesterase, wherein the carbamoyl ester includes an amine group that, upon hydrolysis, becomes at least a component of a pharmacologically active agent, wherein said pharmacologically active agent is an amphetamine compound, further wherein the carbamoyl ester is:

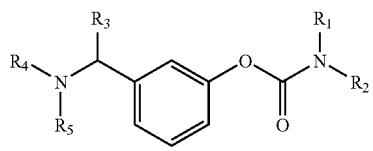

wherein
R₁ is selected from the group consisting of hydrogen, unsubstituted alkyl, substituted alkyl, unsubstituted aralkyl, substituted aralkyl, unsubstituted heteroalkyl, substituted heteroalkyl, unsubstituted heteroaralkyl, substituted heteroaralkyl, unsubstituted aryl, substituted aryl, unsubstituted heteroaryl, substituted heteroaryl, unsubstituted cycloalkyl, substituted cycloalkyl, unsubstituted heterocycloalkyl and substituted heterocycloalkyl;

R₂ is selected from the group consisting of unsubstituted aralkyl and substituted aralkyl, wherein said aralkyl group is an aryl substituent linked by a branched alkyl group having from 3-5 carbon atoms; and R₃, R₄ and R₅ are each, independently or in combination, selected from the group consisting of hydrogen, unsubstituted alkyl, substituted alkyl, unsubstituted aralkyl, substituted aralkyl, unsubstituted heteroalkyl, substituted heteroalkyl, unsubstituted heteroaralkyl, substituted heteroaralkyl, unsubstituted aryl, substituted aryl, unsubstituted heteroaryl, substituted heteroaryl, unsubstituted cycloalkyl, substituted cycloalkyl, unsubstituted heterocycloalkyl and substituted heterocycloalkyl and a pharmaceutically acceptable carrier.

12. The pharmaceutical composition of claim 11, wherein the carbamoyl ester is:

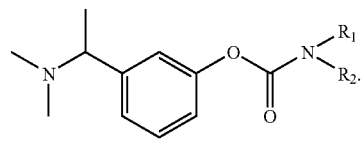

13. The pharmaceutical composition of claim 11, wherein the pharmacologically active agent is selected from amphetamine and methamphetamine.

14. A carbamoyl ester selected from

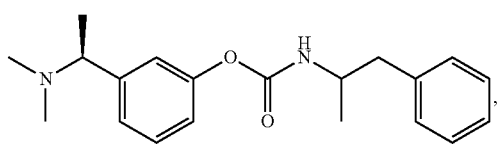

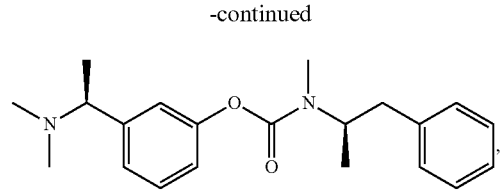

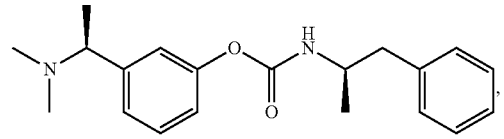

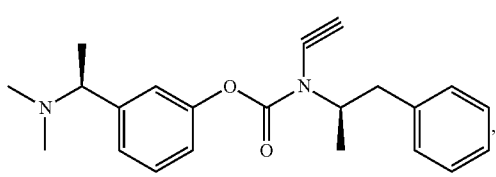

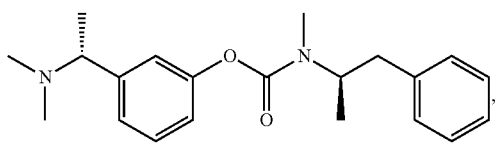

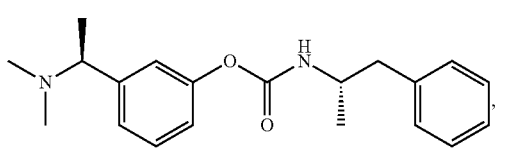

, and

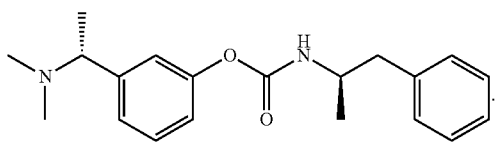

15. A carbamoyl ester

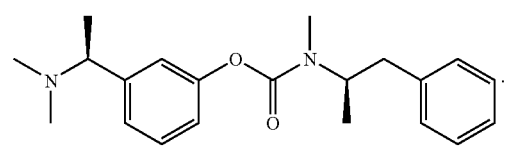

* * * * *

UNITED STATES PATENT AND TRADEMARK OFFICE
CERTIFICATE OF CORRECTION

| | | |
|---|---|---|
| PATENT NO. | : 7,897,639 B2 | Page 1 of 1 |
| APPLICATION NO. | : 10/969796 | |
| DATED | : March 1, 2011 | |
| INVENTOR(S) | : Jeroen C. Verheijen | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 420 days.

Signed and Sealed this
Ninth Day of August, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,897,639 B2 | Page 1 of 1 |
| APPLICATION NO. | : 10/969796 | |
| DATED | : March 1, 2011 | |
| INVENTOR(S) | : Jeroen C. Verheijen et al. | |

It is certified that error appears in the above-identified patent and that said Letters Patent is hereby corrected as shown below:

ON THE TITLE PAGE:

On page 2, column 2, Item (56) References Cited, under the section Other Publications, cancel the text beginning with "Tumiatti et al." to and end "pp. 681-689."

Column 48, claim 14, lines 15-23, the chemical structure

" 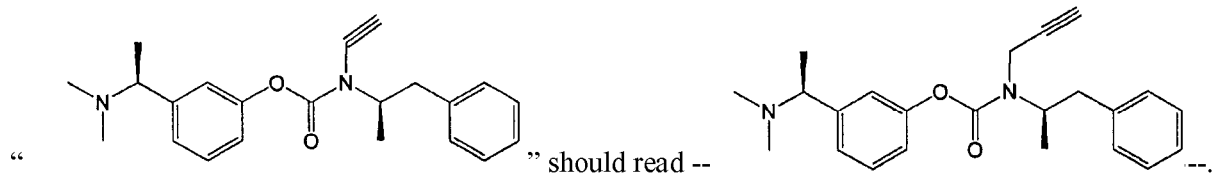 " should read -- --.

Signed and Sealed this
Sixteenth Day of August, 2011

David J. Kappos
*Director of the United States Patent and Trademark Office*